(12) United States Patent
Hoff

(10) Patent No.: US 10,156,554 B1
(45) Date of Patent: Dec. 18, 2018

(54) SYSTEM AND METHOD FOR DETERMINING INFILTRATION OF A BUILDING THROUGH EMPIRICAL TESTING USING A $CO_2$ CONCENTRATION MONITORING DEVICE

(71) Applicant: Clean Power Research, L.L.C., Napa, CA (US)

(72) Inventor: Thomas E. Hoff, Napa, CA (US)

(73) Assignee: CLEAN POWER RESEARCH, L.L.C., Napa, CA (US)

( * ) Notice: Subject to any disclaimer, the term of this patent is extended or adjusted under 35 U.S.C. 154(b) by 313 days.

(21) Appl. No.: 15/138,049

(22) Filed: Apr. 25, 2016

Related U.S. Application Data

(63) Continuation-in-part of application No. 14/664,742, filed on Mar. 20, 2015, which is a continuation of application No. 14/631,798, filed on Feb. 25, 2015.

(51) Int. Cl.
  *G06F 17/50* (2006.01)
  *G01N 33/00* (2006.01)
  *G06F 17/18* (2006.01)
  *G01N 25/18* (2006.01)

(52) U.S. Cl.
  CPC ........... *G01N 33/004* (2013.01); *G01N 25/18* (2013.01); *G01N 33/0062* (2013.01); *G06F 17/18* (2013.01); *G06F 17/5009* (2013.01)

(58) Field of Classification Search
  CPC .. G01N 33/004; G01N 25/18; G01N 33/0062; G06F 17/5009; G06F 17/18
  USPC .......................................................... 703/2
  See application file for complete search history.

(56) References Cited

U.S. PATENT DOCUMENTS

| | | |
|---|---|---|
| 4,089,143 A | 5/1978 | La Pietra |
| 4,992,942 A | 2/1991 | Bauerle et al. |
| 5,001,650 A | 3/1991 | Francis et al. |
| 5,177,972 A | 1/1993 | Sillato et al. |
| 5,602,760 A | 2/1997 | Chacon et al. |
| 5,803,804 A * | 9/1998 | Meier ................. F24F 11/0001 454/256 |
| 6,148,623 A | 11/2000 | Park et al. |

(Continued)

OTHER PUBLICATIONS

Brinkman et al., "Toward a Solar-Powered Grid." IEEE Power & Energy, vol. 9, No. 3, May/Jun. 2011.

(Continued)

*Primary Examiner* — Dwin M Craig
(74) *Attorney, Agent, or Firm* — Patrick J. S. Inouye; Leonid Kisselev

(57) ABSTRACT

A building loses or gains heat through its envelope based on the differential between the indoor and outdoor temperatures. The losses or gains are due to conduction and infiltration. Conventionally, these effects are typically estimated by performing an on-site energy audit. However, total thermal conductivity, conduction, and infiltration can be determined empirically. The number of air changes per hour are empirically measured using a $CO_2$ concentration monitoring device, which enables the infiltration component of total thermal conductivity to be measured directly. The conduction component of thermal conductivity can then be determined by subtracting the infiltration component from the building's total thermal conductivity.

20 Claims, 16 Drawing Sheets

(56) References Cited

U.S. PATENT DOCUMENTS

| | | | |
|---|---|---|---|
| 6,366,889 | B1 | 4/2002 | Zaloom |
| 7,742,892 | B2 | 6/2010 | Fromme et al. |
| 8,155,900 | B1 | 4/2012 | Adams |
| 9,007,460 | B2 | 1/2015 | Schmidt et al. |
| 9,086,585 | B2 | 7/2015 | Hamada et al. |
| 9,098,876 | B2 | 8/2015 | Steven et al. |
| 9,103,719 | B1 | 8/2015 | Ho et al. |
| 9,171,276 | B2 | 10/2015 | Steven et al. |
| 2002/0055358 | A1 | 5/2002 | Hebert |
| 2005/0055137 | A1 | 3/2005 | Andren et al. |
| 2005/0222715 | A1 | 10/2005 | Ruhnke et al. |
| 2007/0084502 | A1 | 4/2007 | Kelly et al. |
| 2008/0258051 | A1 | 10/2008 | Heredia et al. |
| 2009/0125275 | A1 | 5/2009 | Woro |
| 2009/0302681 | A1 | 12/2009 | Yamada et al. |
| 2010/0211222 | A1 | 8/2010 | Ghosh |
| 2010/0219983 | A1 | 9/2010 | Peleg et al. |
| 2011/0137591 | A1 | 6/2011 | Ishibashi |
| 2011/0137763 | A1 | 6/2011 | Aguilar |
| 2011/0272117 | A1 | 11/2011 | Hamstra et al. |
| 2011/0276269 | A1 | 11/2011 | Hummel |
| 2011/0307109 | A1 | 12/2011 | Sri-Jayantha |
| 2012/0130556 | A1 | 5/2012 | Marhoefer |
| 2012/0191439 | A1 | 7/2012 | Meagher et al. |
| 2012/0310416 | A1 | 12/2012 | Tepper et al. |
| 2012/0330626 | A1 | 12/2012 | An et al. |
| 2013/0008224 | A1* | 1/2013 | Stormbom ............ G01N 21/274 73/1.06 |
| 2013/0054662 | A1 | 2/2013 | Coimbra |
| 2013/0060471 | A1 | 3/2013 | Aschheim et al. |
| 2013/0152998 | A1 | 6/2013 | Herzig |
| 2013/0245847 | A1 | 9/2013 | Steven et al. |
| 2013/0262049 | A1 | 10/2013 | Zhang et al. |
| 2014/0039709 | A1 | 2/2014 | Steven et al. |
| 2014/0129197 | A1 | 5/2014 | Sons et al. |
| 2014/0142862 | A1 | 5/2014 | Umeno et al. |
| 2014/0214222 | A1 | 7/2014 | Rouse et al. |
| 2014/0222241 | A1 | 8/2014 | Ols |
| 2014/0278108 | A1 | 9/2014 | Kerrigan et al. |
| 2015/0019034 | A1 | 1/2015 | Gonatas |
| 2015/0057820 | A1 | 2/2015 | Kefayati et al. |
| 2015/0088576 | A1 | 3/2015 | Steven et al. |
| 2015/0112497 | A1 | 4/2015 | Steven et al. |
| 2015/0134251 | A1 | 5/2015 | Bixel |
| 2015/0188415 | A1 | 7/2015 | Abido et al. |
| 2015/0330923 | A1 | 11/2015 | Smullin |
| 2015/0332294 | A1 | 11/2015 | Albert et al. |
| 2016/0140283 | A1 | 5/2016 | Morse et al. |
| 2016/0187911 | A1 | 6/2016 | Carty et al. |
| 2016/0226253 | A1 | 8/2016 | Abido et al. |

OTHER PUBLICATIONS

California ISO. Summary of Preliminary Results of 33% Renewable Integration Study—2010 CPUC LTPP. Docket No. R.10-05-006, May 10, 2011.

Ellis et al., "Model Makers." IEEE Power & Energy, vol. 9, No. 3, May/Jun. 2011.

Danny at al., "Analysis of solar heat gain factors using sky clearness index and energy implications." Energy Conversions and Management, Aug. 2000.

Hoff et al., "Quantifying PV Power Output Variability." Solar Energy 84 (2010) 1782-1793, Oct. 2010.

Hoff et al., "PV Power Output Variability: Calculation of Correlation Coefficients Using Satellite Insolation Data." American Solar Energy Society Annual Conference Proceedings, Raleigh, NC, May 18, 2011.

Kuszamaul et al., "Lanai High-Density Irradiance Sensor Network for Characterizing Solar Resource Variability of MW-Scale PV System." 35th Photovoltaic Specialists Conference, Honolulu, HI. Jun. 20-25, 2010.

Serban C., "Estimating Clear Sky Solar Global Radiation Using Clearness Index, for Brasov Urban Area," Proceedings of the 3rd International Conference on Maritime and Naval Science and Engineering, 2009.

Mills et al., "Dark Shadows." IEEE Power & Energy, vol. 9, No. 3, May/Jun. 2011.

Mills et al., "Implications of Wide-Area Geographic Diversity for Short-Term Variability of Solar Power." Lawrence Berkeley National Laboratory Technical Report LBNL-3884E, Sep. 2010.

Perez et al., "Parameterization of site-specific short-term irradiance variability." Solar Energy, 85 (2011) 1343-1345, Nov. 2010.

Perez et al., "Short-term irradiance variability correlation as a function of distance." Solar Energy, Mar. 2011.

Philip, J., "The Probability Distribution of the Distance Between Two Random Points in a Box." www.math.kth.se/~johanph/habc.pdf. Dec. 2007.

Stein, J., "Simulation of 1-Minute Power Output from Utility-Scale Photovoltaic Generation Systems." American Solar Energy Society Annual Conference Proceedings, Raleigh, NC, May 18, 2011.

Solar Anywhere, 2011. Web-Based Service that Provides Hourly, Satellite-Derived Solar Irradiance Data Forecasted 7 days Ahead and Archival Data back to Jan. 1, 1998. www.SolarAnywhere.com.

Stokes et al., "The atmospheric radiation measurement (ARM) program: programmatic background and design of the cloud and radiation test bed." Bulletin of American Meteorological Society vol. 75, No. 7, pp. 1201-1221, Jul. 1994.

Hoff et al., "Modeling PV Fleet Output Variability," Solar Energy,May 2010.

Olopade at al., "Solar Radiation Characteristics and the performance of Photovoltaic (PV) Modules in a Tropical Station." Journal Sci. Res. Dev. vol. 11, 100-109, 2008/2009.

Li et al. "Analysis of solar heat gain factors using sky clearness index and energy implications." 2000.

Shahab Poshtkouhi et al., "A General Approach for Quantifying the Benefit of Distributed Power Electronics for Fine Grained MPPT in Photovoltaic Applications Using 3-D Modeling," Nov. 20, 2012, IEE Transactions on Poweer Electronics, vol. 27, No. 11, p. 4656-4666.

Pathomthat Chiradeja et al., "An Approaching to Quantify the Technical Benefits of Distributed Generation," Dec. 2004, IEEE Transactions on Energy Conversation, vol. 19, No. 4, p. 764-773.

Mudathir Funsho Akorede et al., "Distributed Energy Resources and Benefits to the Environment," 2010, Renewable and Sustainable Energy Reviews 14, p. 724-734.

V.H. Mendez, et a., "Impact of Distributed Generation on Distribution Investment Deferral," 2006, Electrical Power and Energy Systems 28, p. 244-252.

Francisco M. Gonzalez-Longatt et al., "Impact of Distributed Generation Over Power Losses on Distribution System," Oct. 2007, Electrical Power Quality and Utilization, 9th International Conference.

M. Begovic et al., "Impact of Renewable Distributed Generation on Power Systems," 2001, Proceedings of the 34th Hawaii International Conference on System Sciences, p. 1-10.

M. Thomson et al., "Impact of Widespread Photovoltaics Generation on Distribution Systems," Mar. 2007, IET Renew. Power Gener., vol. 1, No. 1 p. 33-40.

Varun et al., "LCA of Renewable Energy for Electricity Generation Systems—A Review," 2009, Renewable and Sustainable Energy Reviews 12, p. 1067-1073.

Andreas Schroeder, "Modeling Storage and Demand Management in Power Distribution Grids," 2011, Applied Energy 88, p. 4700-4712.

Daniel S. Shugar, "Photovoltaics in the Utility Distribution System: The Evaluation of System and Distributed Benefits," 1990, Pacific Gas and Electric Company Department of Research and Development, p. 836-843.

Thomas Huld, "Estimating Solar Radiation and Photovoltaic System Performance," The PVGIS Approach, 2011 (printed Dec. 13, 2017).

Anderson et al., "Modelling the Heat Dynamics of a Building Using Stochastic Differential Equations," Energy and Building, vol. 31, 2000, pp. 13-24.

(56) References Cited

OTHER PUBLICATIONS

Nguyen et al., "Estimating Potential Photovoltaic Yield With r.sun and the Open Source Geographical Resources Analysis Support System," Mar. 17, 2010, pp. 831-843.
Pless et al., "Procedure for Measuring and Reporting the Performance of Photovoltaic Systems in Buildings," 62 pages, Oct. 2005.
Emery et al., "Solar Cell Efficiency Measurements," Solar Cells, 17 (1986) 253-274.
Santamouris, "Energy Performance of Residential Buildings," James & James/Earchscan, Sterling, VA 2005.
Al-Homoud, "Computer-Aided Building Energy Analysis Techniques," Building & Environment 36 (2001) pp. 421-433.

* cited by examiner

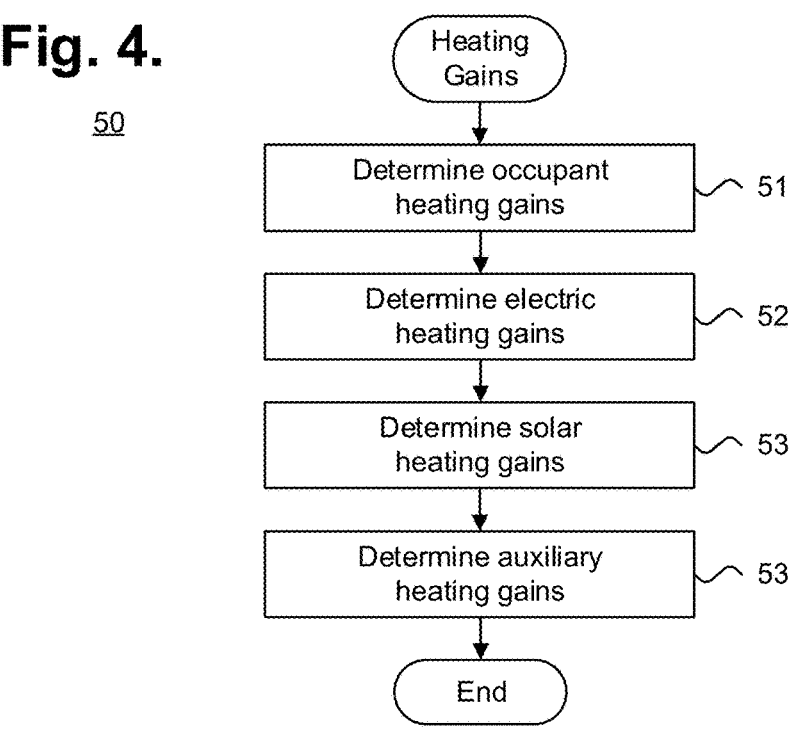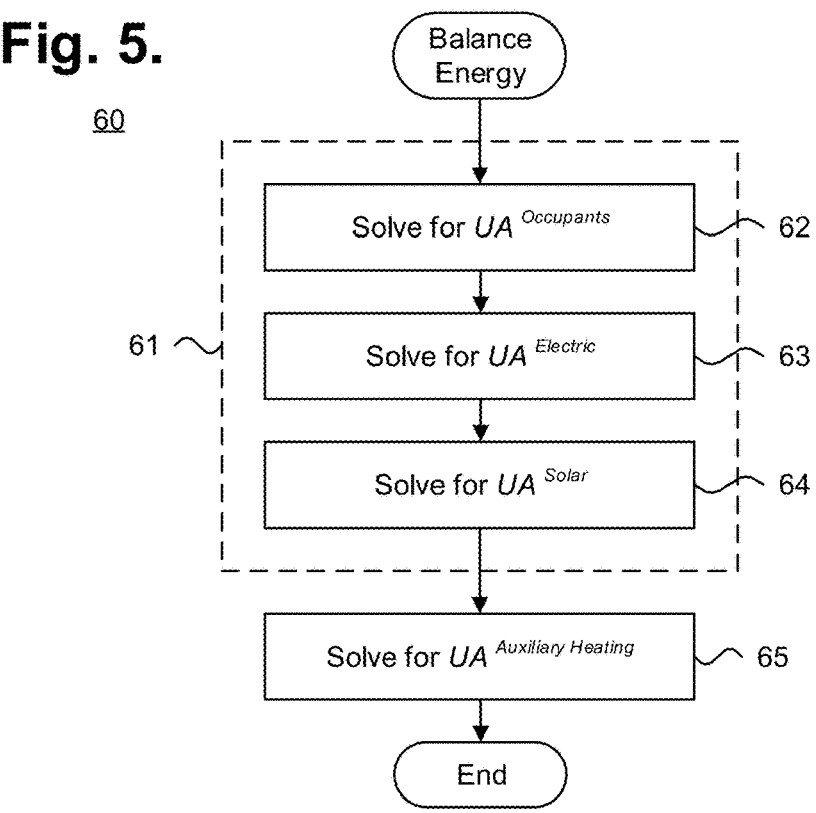

80

| Season | Outdoor Temp. (°F) | Indoor Temp. (°F) | Occupants (People) | Electric (kW) | Solar (kW/m$^2$) | NG Heat (therms) | Elec. Heat (kW) |
|---|---|---|---|---|---|---|---|
| '08-'09 | 50.2 | 61.0 | 5 | 0.905 | 0.133 | 0.069 | 0.000 |
| '09-'10 | 49.1 | 61.0 | 5 | 0.973 | 0.115 | 0.066 | 0.000 |
| '10-'11 | 49.2 | 61.0 | 4 | 0.792 | 0.117 | 0.059 | 0.000 |
| '11-'12 | 48.7 | 61.0 | 4 | 0.845 | 0.144 | 0.068 | 0.000 |
| '12-'13 | 50.4 | 61.0 | 3 | 0.724 | 0.141 | 0.070 | 0.000 |
| '13-'14 | 51.5 | 61.0 | 3 | 0.533 | 0.154 | 0.065 | 0.000 |
| '14-'15 | 55.5 | 66.4 | 2 | 0.391 | 0.120 | 0.000 | 0.418 |

90

| Season | Occupants | Electric | Solar | Aux. Heating | Total |
|---|---|---|---|---|---|
| '08-'09 | 116 | 286 | 105 | 378 | 886 |
| '09-'10 | 105 | 279 | 82 | 327 | 793 |
| '10-'11 | 85 | 229 | 85 | 296 | 695 |
| '11-'12 | 82 | 235 | 100 | 331 | 748 |
| '12-'13 | 71 | 234 | 114 | 391 | 810 |
| '13-'14 | 79 | 192 | 138 | 406 | 815 |
| '14-'15 | 46 | 123 | 94 | 131 | 393 |

100

140

| Test | Desired Parameter | Time to Perform Test | HVAC Status | Electric Heater Status | Require Constant Indoor Temp. | Record Electric Consumption | Record HVAC Status |
|---|---|---|---|---|---|---|---|
| Thermal Conductivity | $UA^{Total}$ | Night | Off | On | Yes | Yes | No |
| Thermal Mass | M | Night | Off | Off | No | Yes | No |
| Effective Window Area | W | Day | Off | Off | No | Yes | No |
| HVAC Efficiency | $\eta^{HVAC}$ | Night | On | Off | No | Yes | Yes |

| Start Time | Data | | | | | Include in Test? | | |
|---|---|---|---|---|---|---|---|---|
| | Outdoor (Measured) | Indoor (Measured) | Solar (VDI) | Consumption (kW) | Occupancy | UATotal | Mass | W |
| 1/29 9:00 PM | 50.5 | 68.3 | 0 | 0.84 | 2 | 0 | 0 | 0 |
| 1/29 10:00 PM | 49.1 | 67.6 | 0 | 0.12 | 2 | 0 | 1 | 0 |
| 1/29 11:00 PM | 47.9 | 67.0 | 0 | 0.12 | 2 | 0 | 1 | 0 |
| 1/30 12:00 AM | 46.8 | 66.5 | 0 | 0.10 | 2 | 0 | 1 | 0 |
| 1/30 1:00 AM | 45.8 | 66.1 | 0 | 0.11 | 2 | 0 | 1 | 0 |
| 1/30 2:00 AM | 44.6 | 65.6 | 0 | 0.29 | 2 | 0 | 1 | 0 |
| 1/30 3:00 AM | 43.7 | 65.2 | 0 | 0.11 | 2 | 0 | 1 | 0 |
| 1/30 4:00 AM | 43.1 | 64.7 | 0 | 0.12 | 2 | 0 | 1 | 0 |
| 1/30 5:00 AM | 42.3 | 64.3 | 0 | 0.10 | 2 | 0 | 1 | 0 |
| 1/30 6:00 AM | 41.5 | 63.8 | 0 | 1.02 | 2 | 0 | 1 | 0 |
| 1/30 7:00 AM | 41.0 | 64.3 | 0 | 2.48 | 2 | 0 | 0 | 0 |
| 1/30 8:00 AM | 42.2 | 64.8 | 200 | 2.04 | 2 | 0 | 0 | 0 |
| 1/30 9:00 AM | 46.6 | 64.5 | 472 | 0.40 | 2 | 0 | 0 | 1 |
| 1/30 10:00 AM | 51.5 | 64.2 | 650 | 0.45 | 2 | 0 | 0 | 1 |
| 1/30 11:00 AM | 54.6 | 64.7 | 761 | 0.62 | 2 | 0 | 0 | 1 |
| 1/30 12:00 PM | 58.5 | 65.4 | 817 | 0.29 | 2 | 0 | 0 | 1 |
| 1/30 1:00 PM | 59.8 | 65.9 | 809 | 0.25 | 2 | 0 | 0 | 1 |
| 1/30 2:00 PM | 60.8 | 66.4 | 744 | 0.25 | 2 | 0 | 0 | 1 |
| 1/30 3:00 PM | 60.8 | 66.7 | 613 | 0.24 | 2 | 0 | 0 | 1 |
| 1/30 4:00 PM | 60.8 | 66.9 | 415 | 0.37 | 2 | 0 | 0 | 1 |
| 1/30 5:00 PM | 60.1 | 67.0 | 143 | 0.95 | 2 | 0 | 0 | 0 |
| 1/30 6:00 PM | 56.7 | 67.2 | 0 | 1.33 | 2 | 0 | 0 | 0 |
| 1/30 7:00 PM | 53.8 | 67.1 | 0 | 1.41 | 2 | 1 | 0 | 0 |
| 1/30 8:00 PM | 53.1 | 67.2 | 0 | 1.49 | 2 | 1 | 0 | 0 |
| 1/30 9:00 PM | 53.1 | 67.2 | 0 | 1.50 | 2 | 1 | 0 | 0 |
| 1/30 10:00 PM | 53.1 | 67.1 | 0 | 1.45 | 2 | 1 | 0 | 0 |
| 1/30 11:00 PM | 53.1 | 66.9 | 0 | 1.35 | 3 | 1 | 0 | 0 |
| 1/31 12:00 AM | 53.1 | 66.6 | 0 | 1.34 | 3 | 1 | 0 | 0 |
| 1/31 1:00 AM | 53.1 | 66.5 | 0 | 1.35 | 3 | 1 | 0 | 0 |
| 1/31 2:00 AM | 53.1 | 66.5 | 0 | 1.48 | 3 | 1 | 0 | 0 |
| 1/31 3:00 AM | 53.1 | 66.7 | 0 | 1.99 | 3 | 1 | 0 | 0 |
| 1/31 4:00 AM | 53.1 | 67.0 | 0 | 1.99 | 3 | 1 | 0 | 0 |
| 1/31 5:00 AM | 53.1 | 67.1 | 0 | 1.57 | 3 | 1 | 0 | 0 |
| 1/31 6:00 AM | 54.1 | 66.9 | 0 | 1.20 | 3 | 0 | 0 | 0 |

| Parameter Estimation | UATotal Test | Mass Test | Window Test |
|---|---|---|---|
| Test Start Time | 1/30 7:00PM | 1/29 10:00PM | 1/30 9:00AM |
| Test End Time | 1/31 6:00AM | 1/30 7:00AM | 1/30 5:00PM |
| Number of Hours | 11 | 9 | 8 |
| Starting Indoor Temperature (°F) | 67.1 | 67.6 | 64.5 |
| Ending Indoor Temperature (°F) | 67.1 | 63.8 | 66.9 |
| Average Indoor Temperature (°F) | 66.9 | 65.7 | 65.6 |
| Average Outdoor Temperature (°F) | 53.2 | 45.0 | 56.7 |
| Avg. Solar (kW/m^2) | 0.00 | 0.00 | 0.66 |
| Avg. Power Consumption (kW) | 1.54 | 0.23 | 0.36 |
| Avg. Occupancy (people) | 2.6 | 2.0 | 2.0 |
| Indoor/Outdoor Delta T (°F) | 13.75 | 20.67 | 8.92 |
| Indoor Finish/Start Delta T (°F) | 0.0 | -3.8 | 2.5 |
|  |  |  |  |
|  | UATotal (Btu/h-°F) | Mass (Btu/°F) | w (m$^2$) |
| Results | 429 | 18,080 | 3.40 |

Fig. 20.

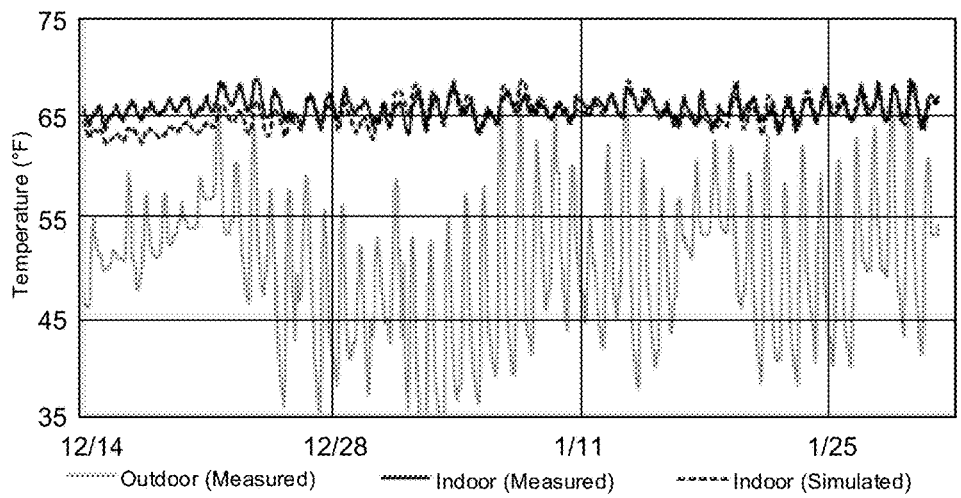

240

250

260

270

280

290

SYSTEM AND METHOD FOR DETERMINING INFILTRATION OF A BUILDING THROUGH EMPIRICAL TESTING USING A $CO_2$ CONCENTRATION MONITORING DEVICE

CROSS-REFERENCE TO RELATED APPLICATIONS

This patent application is a continuation-in-part of U.S. patent application Ser. No. 14/664,742, filed Mar. 20, 2015, pending, which is a continuation of U.S. patent application Ser. No. 14/631,798, filed Feb. 25, 2015, pending, the priority dates of which are claimed and the disclosures of which are incorporated by reference.

FIELD

This application relates in general to energy conservation and, in particular, to a system and method for determining infiltration of a building through empirical testing using a $CO_2$ concentration monitoring device.

BACKGROUND

The cost of energy has continued to steadily rise as power utilities try to cope with continually growing demands, increasing fuel prices, and stricter regulatory mandates. Power utilities must maintain existing power generation and distribution infrastructure, while simultaneously finding ways to add more capacity to meet future needs, both of which add to costs. Burgeoning energy consumption continues to impact the environment and deplete natural resources.

A major portion of rising energy costs is borne by consumers, who, despite the need, lack the tools and wherewithal to identify the most cost effective ways to appreciably lower their energy consumption. For instance, no-cost behavioral changes, such as adjusting thermostat settings and turning off unused appliances, and low-cost physical improvements, such as switching to energy-efficient light bulbs, may be insufficient. Moreover, as space heating and air conditioning together consume the most energy in the average home, appreciable decreases in energy consumption can usually only be achieved by making costly upgrades to a building's heating or cooling envelope or "shell." However, identifying those improvements that will yield an acceptable return on investment in terms of costs versus energy savings requires first determining building-specific parameters, including thermal conductivity ($UA^{Total}$) and infiltration.

Heating, ventilating, and air conditioning (HVAC) energy costs are directly tied to a building's thermal conductivity. A poorly insulated home or a leaky building will require more HVAC usage to maintain a desired interior temperature than would a comparably-sized but well-insulated and sealed structure. Reducing HVAC energy costs, though, is not as simple as merely choosing a thermostat setting that causes an HVAC system to run for less time or less often. Rather, numerous factors, including thermal conductivity, HVAC system efficiency, heating or cooling season durations, and indoor and outdoor temperature differentials all weigh into energy consumption and need be taken into account when seeking an effective yet cost efficient HVAC energy solution.

Conventionally, an on-site energy audit is performed to determine a building's thermal conductivity $UA^{Total}$. An energy audit is a labor intensive and intrusive process that involves measuring a building's physical dimensions; approximating insulation R-values; detecting air leakage; and estimating infiltration through a blower door test. A numerical model is run against the audit findings to solve for thermal conductivity. The $UA^{Total}$ is combined with heating and cooling season durations and adjusted for HVAC system efficiency, plus any solar or non-utility supplied power savings fraction. An audit report is then presented as a checklist of steps that may be taken to improve the building's shell.

The blower door test part of the audit presents several challenges. Before the test, monitoring equipment must be calibrated on-site to building-specific factors and airtight covers must be placed over all HVAC vents. Exterior doors, windows and other openings must also be sealed and a blower door panel will be temporarily placed into an outside doorway. During the test, a fan in the blower door panel forces air into or pulls air out of the building to respectively generate a positive or negative pressure differential to the outdoors, and pressure differences are measured. Following completion, test results are converted into pressure values representing normal conditions from which infiltration is then estimated.

As an involved process, a blower door test can be costly, time-consuming, and invasive for building owners and occupants. Throughout the test, trained personnel must be on-site. As well, the building is rendered temporarily uninhabitable and must remain closed up for an extended period of time while a noisy blower fan is run. In addition, a blower door test requires specialized equipment and trained personnel, which adds to the cost. Notwithstanding, blower door test results are fallible and are simply estimates. Calibration errors that can invalidate a test can and do occur; moreover, testing results need to be translated from high pressure testing conditions to normative building operating conditions with reliance on an approximation that projects infiltration losses.

Therefore, a need remains for a practical model for determining actual and potential energy consumption for the heating and cooling of a building.

A further need remains for an approach to estimating structural infiltration without the costs and inconvenience of blower door testing methodologies.

SUMMARY

Fuel consumption for building heating and cooling can be calculated through two practical approaches that characterize a building's thermal efficiency through empirically-measured values and readily-obtainable energy consumption data, such as available in utility bills, thereby avoiding intrusive and time-consuming analysis with specialized testing equipment. While the discussion is herein centered on building heating requirements, the same principles can be applied to an analysis of building cooling requirements. The first approach can be used to calculate annual or periodic fuel requirements. The approach requires evaluating typical monthly utility billing data and approximations of heating (or cooling) losses and gains.

The second approach can be used to calculate hourly (or interval) fuel requirements. The approach includes empirically deriving three building-specific parameters: thermal mass, thermal conductivity, and effective window area. HVAC system power rating and conversion and delivery efficiency are also parametrized. The parameters are estimated using short duration tests that last at most several days. The parameters and estimated HVAC system efficiency are used to simulate a time series of indoor building temperature. In addition, the second hourly (or interval) approach can be used to verify or explain the results from the first annual (or periodic) approach. For instance, time series results can be calculated using the second approach over the span of an entire year and compared to results determined through the first approach. Other uses of the two approaches and forms of comparison are possible.

A building loses or gains heat through its envelope based on the differential between the indoor and outdoor temperatures. The losses or gains are due to conduction and infiltration. Conventionally, these effects are typically estimated by performing an on-site energy audit. However, total thermal conductivity, conduction, and infiltration can be determined empirically. The number of air changes per hour are empirically measured using a $CO_2$ concentration monitoring device, which enables the infiltration component of total thermal conductivity to be measured directly. The conduction component of thermal conductivity can then be determined by subtracting the infiltration component from the building's total thermal conductivity.

One embodiment provides a system and method for determining infiltration of a building through empirical testing using a $CO_2$ concentration monitoring device. Baseline $CO_2$ concentration outside a building under test is chosen. Initial $CO_2$ concentration inside the building is determined and recorded using a $CO_2$ concentration monitoring device. $CO_2$ concentration is increased over the initial $CO_2$ concentration. Sources causing increase in the $CO_2$ concentration inside the building are negated and thereafter further $CO_2$ concentrations are measured and recorded inside the building using the $CO_2$ concentration monitoring device until the further $CO_2$ concentrations substantially stabilize. Infiltration of the building is determined based on a number of air changes as a function of the difference of the initial $CO_2$ concentration less the baseline $CO_2$ concentration over one or more of the further $CO_2$ concentration at a given time less the baseline $CO_2$ concentration and the given time.

The foregoing approaches, annual (or periodic) and hourly (or interval) improve upon and compliment the standard energy audit-style methodology of estimating heating (and cooling) fuel consumption in several ways. First, per the first approach, the equation to calculate annual fuel consumption and its derivatives is simplified over the fully-parameterized form of the equation used in energy audit analysis, yet without loss of accuracy. Second, both approaches require parameters that can be obtained empirically, rather than from a detailed energy audit that requires specialized testing equipment and prescribed test conditions. Third, per the second approach, a time series of indoor temperature and fuel consumption data can be accurately generated. The resulting fuel consumption data can then be used by economic analysis tools using prices that are allowed to vary over time to quantify economic impact.

Moreover, the economic value of heating (and cooling) energy savings associated with any building shell improvement in any building has been shown to be independent of building type, age, occupancy, efficiency level, usage type, amount of internal electric gains, or amount solar gains, provided that fuel has been consumed at some point for auxiliary heating. The only information required to calculate savings includes the number of hours that define the winter season; average indoor temperature; average outdoor temperature; the building's HVAC system efficiency (or coefficient of performance for heat pump systems); the area of the existing portion of the building to be upgraded; the R-value of the new and existing materials; and the average price of energy, that is, heating fuel.

The $CO_2$ monitoring device described and applied herein can replace the blower door test component of an on-site energy audit to baseline infiltration. Use of the device can also be incorporated into the measurement and evaluation (M&E) portion of a utility's energy efficiency program to verify the effectiveness of building sealing initiatives.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE DRAWINGS

FIG. 4 is a flow diagram showing a routine for determining heating gains for use in the method of FIG. 3.

FIG. 5 is a flow diagram showing a routine for balancing energy for use in the method of FIG. 3.

FIG. 18 is a table showing, by way of example, test data.

FIG. 19 is a table showing, by way of example, the statistics performed on the data in the table of FIG. 18 required to calculate the three test parameters.

FIG. 20 is a graph showing, by way of example, hourly indoor (measured and simulated) and outdoor (measured) temperatures.

DETAILED DESCRIPTION

Conventional Energy Audit-Style Approach

Figure 1:
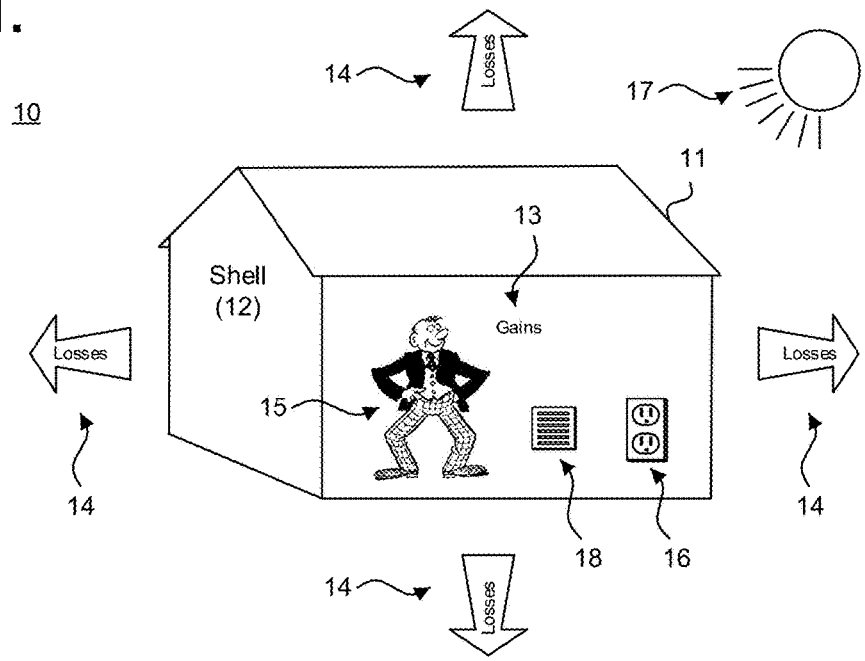
FIG. 1 is a functional block diagram showing heating losses and gains relative to a structure.

Conventionally, estimating periodic HVAC energy consumption and therefore fuel costs includes analytically determining a building's thermal conductivity ($UA^{Total}$) based on results obtained through an on-site energy audit. For instance, J. Randolf and G. Masters, *Energy for Sustainability: Technology, Planning, Policy*, pp. 247, 248, 279 (2008), present a typical approach to modeling heating energy consumption for a building, as summarized therein by Equations 6.23, 6.27, and 7.5. The combination of these equations states that annual heating fuel consumption $Q^{Fuel}$ equals the product of $UA^{Total}$, 24 hours per day, and the number of heating degree days (HDD) associated with a particular balance point temperature $T^{Balance\ Point}$, as adjusted for the solar savings fraction (SSF) (or non-utility supplied power savings fraction) divided by HVAC system efficiency ($\eta^{HVAC}$):

$$Q^{Fuel} = (UA^{Total})(24*HDD^{T^{Balance\ Point}})(1-SSF)\left(\frac{1}{\eta^{HVAC}}\right) \quad (1)$$

such that:

$$T^{Balance\ Point} = T^{Set\ Point} - \frac{Internal\ Gains}{UA^{Total}} \quad (2)$$

and $$\eta^{HVAC} = \eta^{Furnace}\eta_{Distribution} \quad (3)$$

where $T^{Set\ Point}$ represents the temperature setting of the thermostat, Internal Gains represents the heating gains experienced within the building as a function of heat generated by internal sources and auxiliary heating, as further discussed infra, $\eta^{Furnace}$ represents the efficiency of the furnace or heat source proper, and $\eta^{Distribution}$ represents the efficiency of the duct work and heat distribution system. For clarity $HDD^{T^{Balance\ Point}}$ will be abbreviated to $HDD^{Balance\ Point\ Temp}$.

A cursory inspection of Equation (1) implies that annual fuel consumption is linearly related to a building's thermal conductivity. This implication further suggests that calculating fuel savings associated with building envelope or shell improvements is straightforward. In practice, however, such calculations are not straightforward because Equation (1) was formulated with the goal of determining the fuel required to satisfy heating energy needs. As such, there are several additional factors that the equation must take into consideration.

First, Equation (1) needs to reflect the fuel that is required only when indoor temperature exceeds outdoor temperature. This need led to the heating degree day (HDD) approach (or could be applied on a shorter time interval basis of less than one day) of calculating the difference between the average daily (or hourly) indoor and outdoor temperatures and retaining only the positive values. This approach complicates Equation (1) because the results of a non-linear term must be summed, that is, the maximum of the difference between average indoor and outdoor temperatures and zero. Non-linear equations complicate integration, that is, the continuous version of summation.

Second, Equation (1) includes the term Balance Point temperature ($T^{Balance\ Point}$) The goal of including the term $T^{Balance\ Point}$ was to recognize that the internal heating gains of the building effectively lowered the number of degrees of temperature that auxiliary heating needed to supply relative to the temperature setting of the thermostat $T^{Set\ Point}$. A balance point temperature $T^{Balance\ Point}$ of 65° F. was initially selected under the assumption that 65° F. approximately accounted for the internal gains. As buildings became more efficient, however, an adjustment to the balance point temperature $T^{Balance\ Point}$ was needed based on the building's thermal conductivity ($UA^{Total}$) and internal gains. This assumption further complicated Equation (1) because the equation became indirectly dependent on (and inversely related to) $UA^{Total}$ through $T^{Balance\ Point}$.

Third, Equation (1) addresses fuel consumption by auxiliary heating sources. As a result, Equation (1) must be adjusted to account for solar gains. This adjustment was accomplished using the Solar Savings Fraction (SSF). The SSF is based on the Load Collector Ratio (see Eq. 7.4 in Randolf and Masters, p. 278, cited supra, for information about the LCR). The LCR, however, is also a function of $UA^{Total}$. As a result, the SSF is a function of $UA^{Total}$ in a complicated, non-closed form solution manner. Thus, the SSF further complicates calculating the fuel savings associated with building shell improvements because the SSF is indirectly dependent on $UA^{Total}$.

As a result, these direct and indirect dependencies in Equation (1) significantly complicate calculating a change in annual fuel consumption based on a change in thermal conductivity. The difficulty is made evident by taking the derivative of Equation (1) with respect to a change in thermal conductivity. The chain and product rules from calculus need to be employed since $HDD^{Balance\ Point\ Temp}$ and SSF are indirectly dependent on $UA^{Total}$:

$$\frac{dQ^{Fuel}}{dUA^{Total}}\left\{(UA^{Total})\left[(HDD^{Balance\ Point\ Temp})\left(-\frac{dSSF}{dLCR}\frac{dLCR}{dUA^{Total}}\right)+\right.\right. \quad (4)$$
$$\left.\left(\frac{dHDD^{Balance\ Point\ Temp}}{dT^{Balance\ Point}}\frac{dT^{Balance\ Point}}{dUA^{Total}}\right)(1-SSF)\right]+$$
$$\left.(HDD^{Balance\ Point\ Temp})(1-SSF)\right\}\left(\frac{24}{\eta^{HVAC}}\right)$$

The result is Equation (4), which is an equation that is difficult to solve due to the number and variety of unknown inputs that are required.

To add even further complexity to the problem of solving Equation (4), conventionally, $UA^{Total}$ is determined analytically by performing a detailed energy audit of a building. An energy audit involves measuring physical dimensions of walls, windows, doors, and other building parts; approximating R-values for thermal resistance; estimating infiltration using a blower door test; and detecting air leakage. A numerical model is then run to perform the calculations necessary to estimate total thermal conductivity. Such an energy audit can be costly, time consuming, and invasive for building owners and occupants. Moreover, as a calculated result, the value estimated for $UA^{Total}$ carries the potential for inaccuracies, as the model is strongly influenced by physical mismeasurements or omissions, data assumptions, and so forth.

Empirically-Based Approaches to Modeling Heating Fuel Consumption

A building loses or gains heat through its envelope based on the differential between the indoor and outdoor temperatures. The losses or gains are due to conduction and infiltration. Conventionally, these effects are typically estimated by performing an on-site energy audit. However, total thermal conductivity, conduction, and infiltration can be determined empirically. In one embodiment, building heating (and cooling) fuel consumption can be calculated through empirical two approaches, annual (or periodic) and hourly (or interval), to thermally characterize a building without intrusive and time-consuming tests. The first approach, referred to as a Virtual Energy Audit, as further described infra beginning with reference to FIG. 1, can be performed without placing any equipment on-site and only requires typical monthly utility billing data and approximations of heating (or cooling) losses and gains. The second approach, referred to as a Lean Energy Audit, as further described infra beginning with reference to FIG. 11, requires placing minimal monitoring equipment on-site and involves empirically deriving three building-specific parameters, thermal mass, thermal conductivity, and effective window area, plus HVAC system efficiency using short duration tests that last at most several days. The three building-specific parameters thus obtained can then be used to simulate a time series of indoor building temperature, seasonal fuel consumption, and maximum indoor temperature.

Figure 22:
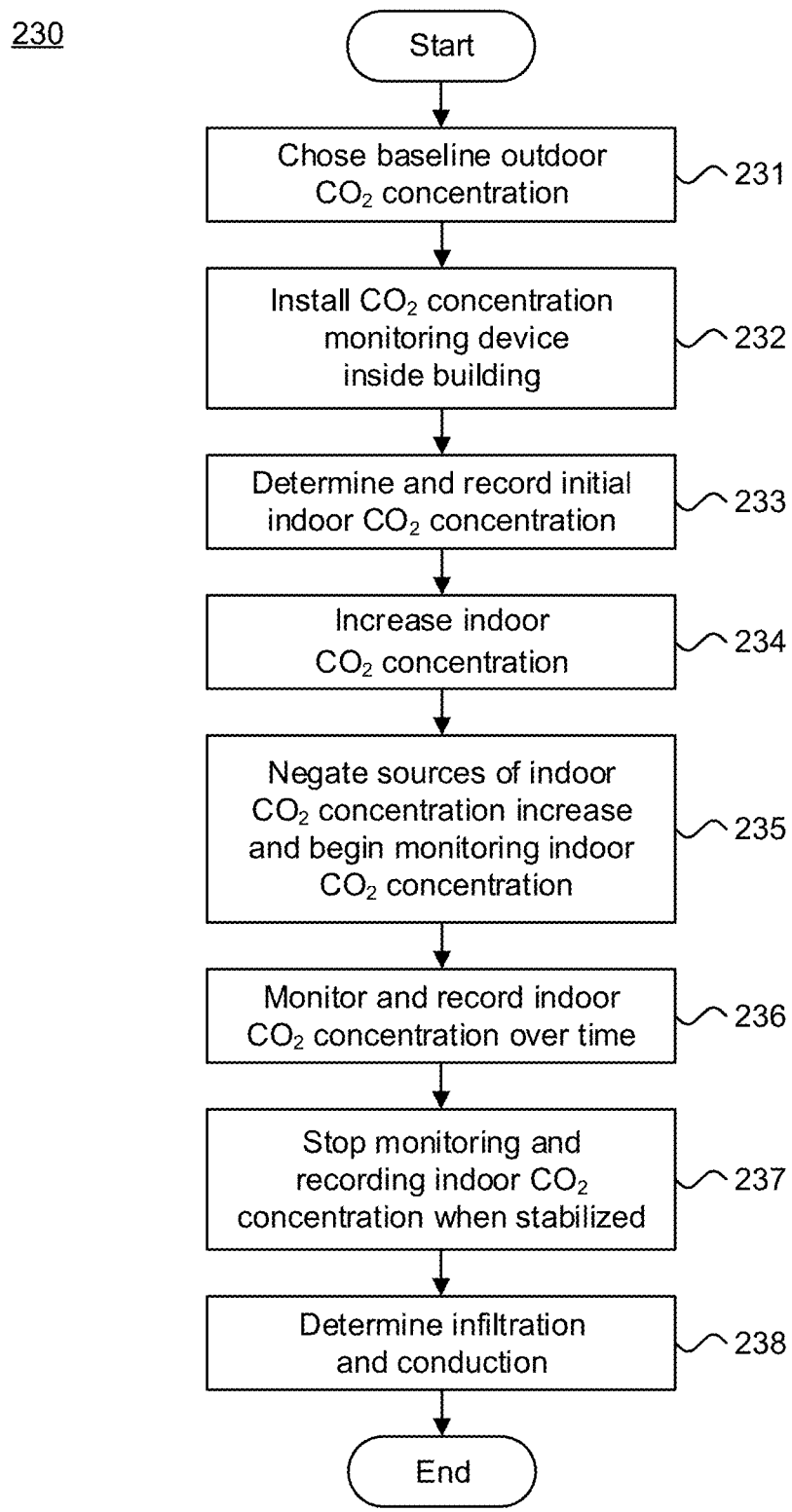
FIG. 22 is a flow diagram showing a method for determining infiltration of a building through empirical testing using a $CO_2$ concentration monitoring device, in accordance with a further embodiment.

The Virtual Energy Audit and Lean Energy Audit approaches empirically measure total thermal conductivity $UA^{Total}$. As described, for instance, in commonly-assigned U.S. Patent application, entitled "Computer-Implemented System and Method for Interactively Evaluating Personal Energy-Related Investments," Ser. No. 14/294,079, filed Jun. 2, 2014, pending, the disclosure of which is incorporated by reference, $UA^{Total}$ equals heat loss or gain due to conduction plus infiltration, which can be formulaically expressed as:

$$UA^{Total}=\overbrace{\left(\sum_{i=1}^{N}U^{i}A^{i}\right)}^{Conduction}+\overbrace{\rho c n V}^{Infiltration} \quad (5)$$

where $U^i$ represents the inverse of the R-value and $A^i$ represents the area of surface i; $\rho$ is a constant that represents the density of air (lbs./ft$^3$); c is a constant that represents the specific heat of air (Btu/lb.-° F.); n is the number of air changes per hour (ACH); and V represents the volume of air per air change (ft$^3$/AC). The density of air $\rho$ and the specific heat of air c are the same for all buildings and respectively equal 0.075 lbs./ft$^3$ and 0.24 Btu/lb.-° F. The number of ACH n and the volume of air per air change V are building-specific values. Volume V can be measured directly or can be approximated by multiplying building square footage times the average room height. Number of ACH n can be estimated using a blower door test, such as described supra. Alternatively, in a further embodiment, the number of ACH n can be empirically measured under actual operating conditions, as further described infra beginning with reference to FIG. 22, which enables the infiltration component of total thermal conductivity to be measured directly. The conduction component of thermal conductivity can then be determined by subtracting the infiltration component from the building's total thermal conductivity.

While the discussion herein is centered on building heating requirements, the same principles can be applied to an analysis of building cooling requirements. In addition, conversion factors for occupant heating gains (250 Btu of heat per person per hour), heating gains from internal electricity consumption (3,412 Btu per kWh), solar resource heating gains (3,412 Btu per kWh), and fuel pricing ($\frac{Price^{NG}}{10^5}$ if in units of $ per therm and $\frac{Price^{Electrity}}{3,412}$ if in units of $ per kWh) are used by way of example; other conversion factors or expressions are possible.

First Approach: Annual (or Periodic) Fuel Consumption

Fundamentally, thermal conductivity is the property of a material, here, a structure, to conduct heat. -71- is a functional block diagram 10 showing heating losses and gains relative to a structure 11. Inefficiencies in the shell 12 (or envelope) of a structure 11 can result in losses in interior heating 14, whereas gains 13 in heating generally originate either from sources within (or internal to) the structure 11, including heating gains from occupants 15, gains from operation of electric devices 16, and solar gains 17, or from auxiliary heating sources 18 that are specifically intended to provide heat to the structure's interior.

In this first approach, the concepts of balance point temperatures and solar savings fractions, per Equation (1), are eliminated. Instead, balance point temperatures and solar savings fractions are replaced with the single concept of balance point thermal conductivity. This substitution is made by separately allocating the total thermal conductivity of a building ($UA^{Total}$) to thermal conductivity for internal heating gains ($UA^{Balance\ Point}$) including occupancy, heat produced by operation of certain electric devices, and solar gains, and thermal conductivity for auxiliary heating ($UA^{Auxiliary\ Heating}$). The end result is Equation (35), further discussed in detail infra, which eliminates the indirect and non-linear parameter relationships in Equation (1) to $UA^{Total}$.

Figure 2:
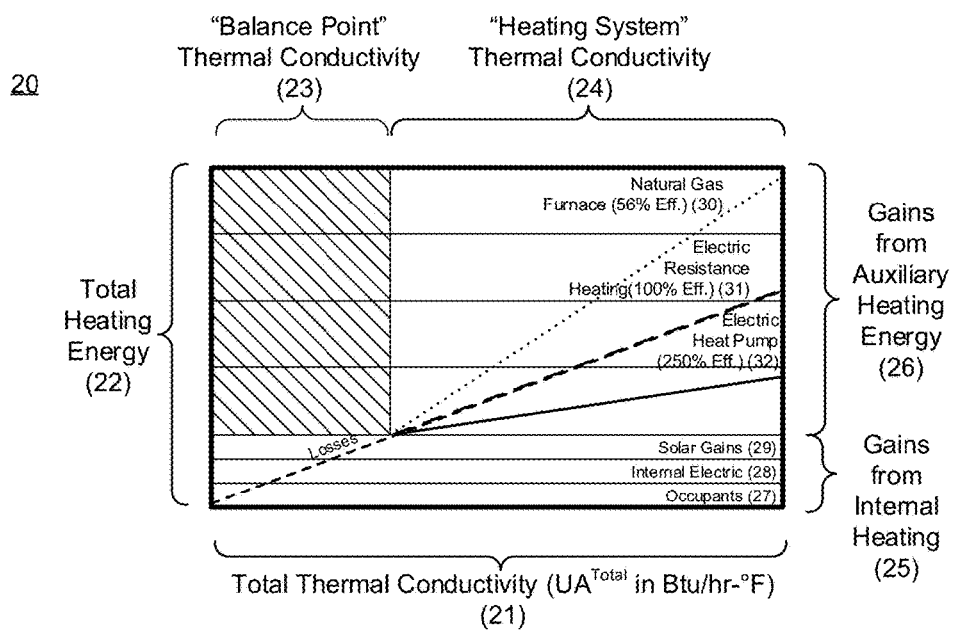
FIG. 2 is a graph showing, by way of example, balance point thermal conductivity.

The conceptual relationships embodied in Equation (35) can be described with the assistance of a diagram. FIG. 2 is a graph 20 showing, by way of example, balance point thermal conductivity $UA^{Balance\ Point}$, that is, the thermal conductivity for internal heating gains. The x-axis 21 represents total thermal conductivity, $UA^{Total}$, of a building (in units of Btu/hr-° F.). The y-axis 22 represents total heating energy consumed to heat the building. Total thermal conductivity 21 (along the x-axis) is divided into "balance point" thermal conductivity ($UA^{Balance\ Point}$) 23 and "heating system" (or auxiliary heating) thermal conductivity ($UA^{Auxiliary\ Heating}$) 24. "Balance point" thermal conductivity 23 characterizes heating losses, which can occur, for example, due to the escape of heat through the building envelope to the outside and by the infiltration of cold air through the building envelope into the building's interior that are compensated for by internal gains. "Heating system" thermal conductivity 24 characterizes heating gains, which reflects the heating delivered to the building's interior above the balance point temperature $T^{Balance\ Point}$, generally as determined by the setting of the auxiliary heating source's thermostat or other control point.

In this approach, total heating energy 22 (along the y-axis) is divided into gains from internal heating 25 and gains from auxiliary heating energy 25. Internal heating gains are broken down into heating gains from occupants 27, gains from operation of electric devices 28 in the building, and solar gains 29. Sources of auxiliary heating energy include, for instance, natural gas furnace 30 (here, with a 56% efficiency), electric resistance heating 31 (here, with a 100% efficiency), and electric heat pump 32 (here, with a 250% efficiency). Other sources of heating losses and gains are possible.

Figure 3:
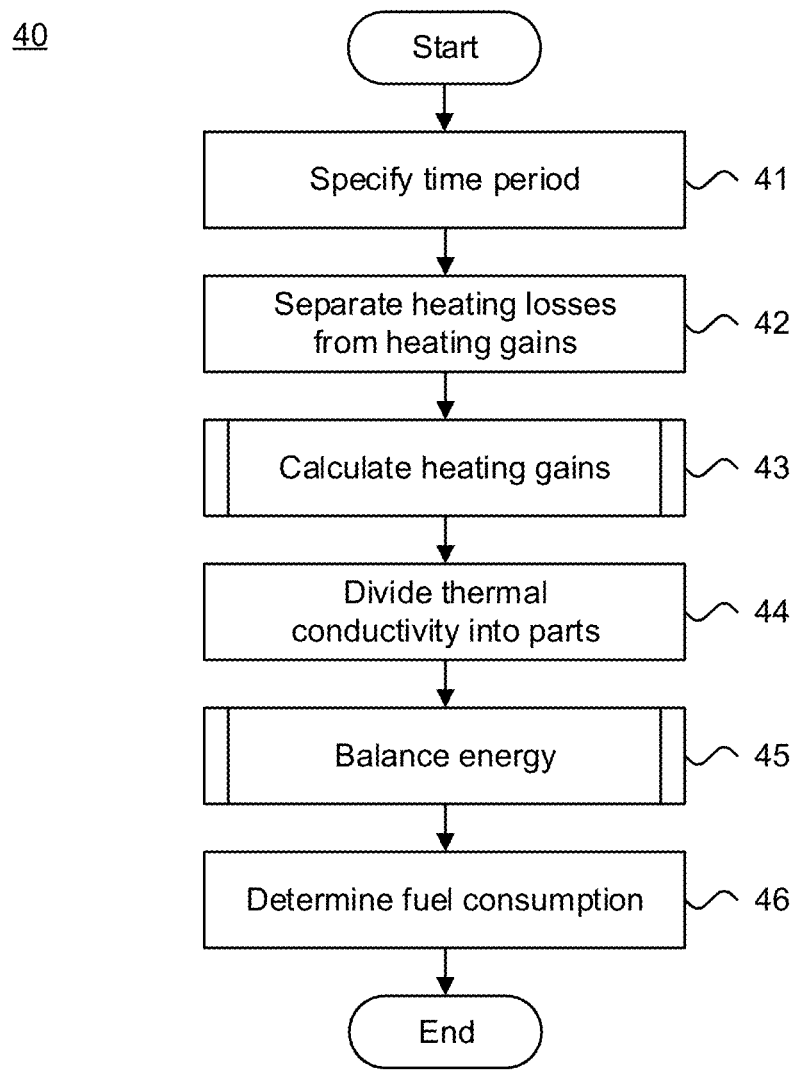
FIG. 3 is a flow diagram showing a computer-implemented method for modeling periodic building heating energy consumption in accordance with one embodiment.

The first approach provides an estimate of fuel consumption over a year or other period of inquiry based on the separation of thermal conductivity into internal heating gains and auxiliary heating. FIG. 3 is a flow diagram showing a computer-implemented method 40 for modeling periodic building heating energy consumption in accordance with one embodiment. Execution of the software can be performed with the assistance of a computer system, such as further described infra with reference to FIG. 29, as a series of process or method modules or steps.

In the first part of the approach (steps 41-43), heating losses and heating gains are separately analyzed. In the second part of the approach (steps 44-46), the portion of the heating gains that need to be provided by fuel, that is, through the consumption of energy for generating heating using auxiliary heating 18 (shown in -71-), is determined to yield a value for annual (or periodic) fuel consumption. Each of the steps will now be described in detail.

Specify Time Period

Heating requirements are concentrated during the winter months, so as an initial step, the time period of inquiry is specified (step 41). The heating degree day approach (HDD) in Equation (1) requires examining all of the days of the year and including only those days where outdoor temperatures are less than a certain balance point temperature. However, this approach specifies the time period of inquiry as the winter season and considers all of the days (or all of the hours, or other time units) during the winter season. Other periods of inquiry are also possible, such as a five- or ten-year time frame, as well as shorter time periods, such as one- or two-month intervals.

Separate Heating Losses from Heating Gains

Heating losses are considered separately from heating gains (step 42). The rationale for drawing this distinction will now be discussed.

Heating Losses

For the sake of discussion herein, those regions located mainly in the lower latitudes, where outdoor temperatures remain fairly moderate year round, will be ignored and focus placed instead on those regions that experience seasonal shifts of weather and climate. Under this assumption, a heating degree day (HDD) approach specifies that outdoor temperature must be less than indoor temperature. No such limitation is applied in this present approach. Heating losses are negative if outdoor temperature exceeds indoor temperature, which indicates that the building will gain heat during these times. Since the time period has been limited to only the winter season, there will likely to be a limited number of days when that situation could occur and, in those limited times, the building will benefit by positive heating gain. (Note that an adjustment would be required if the building took advantage of the benefit of higher outdoor temperatures by circulating outdoor air inside when this condition occurs. This adjustment could be made by treating the condition as an additional source of heating gain.)

As a result, fuel consumption for heating losses $Q^{Losses}$ over the winter season equals the product of the building's total thermal conductivity $UA^{Total}$ and the difference between the indoor $T^{Indoor}$ and outdoor temperature $T^{Outdoor}$, summed over all of the hours of the winter season:

$$Q^{Losses} = \sum_{t,Start}^{t,End} (UA^{Total})(T_t^{Indoor} - T_t^{Outdoor}) \quad (6)$$

where Start and End respectively represent the first and last hours of the winter (heating) season.

Equation (6) can be simplified by solving the summation. Thus, total heating losses $Q^{Losses}$ equal the product of thermal conductivity $UA^{Total}$ and the difference between average indoor temperature $\overline{T}^{Indoor}$ and average outdoor temperature $\overline{T}^{Outdoor}$ over the winter season and the number of hours H in the season over which the average is calculated:

$$Q^{Losses} = (UA^{Total})(\overline{T}^{Indoor} - \overline{T}^{Outdoor})(H) \quad (7)$$

Heating Gains

Heating gains are calculated for two broad categories (step 43) based on the source of heating, internal heating gains $Q^{Gains-Internal}$ and auxiliary heating gains $Q^{Gains-Auxiliary\ Heating}$, as further described infra with reference to FIG. 4.

Internal heating gains can be subdivided into heating gained from occupants $Q^{Gains\text{-}Occupants}$, heating gained from the operation of electric devices $Q^{Gains\text{-}Electric}$, and heating gained from solar heating $Q^{Gains\text{-}Solar}$. Other sources of internal heating gains are possible. The total amount of heating gained $Q^{Gains}$ from these two categories of heating sources equals:

$$Q^{Gains} = Q^{Gains\text{-}Internal} + Q^{Gains\text{-}Auxiliary\ Heating} \tag{8}$$

where $$Q^{Gains\text{-}Internal} = Q^{Gains\text{-}Occupants} + Q^{Gains\text{-}Electric} + Q^{Gains\text{-}Solar} \tag{9}$$

Calculate Heating Gains

Equation (9) states that internal heating gains $Q^{Gains\text{-}Internal}$ include heating gains from Occupant, Electric, and Solar heating sources. FIG. 4 is a flow diagram showing a routine 50 for determining heating gains for use in the method 40 of FIG. 3 Each of these heating gain sources will now be discussed.

Occupant Heating Gains

People occupying a building generate heat. Occupant heating gains $Q^{Gains\text{-}Occupants}$ (step 51) equal the product of the heat produced per person, the average number of people in a building over the time period, and the number of hours (H) (or other time units) in that time period. Let $\overline{P}$ represent the average number of people. For instance, using a conversion factor of 250 Btu of heat per person per hour, heating gains from the occupants $Q^{Gains\text{-}Occupants}$ equal:

$$Q^{Gains\text{-}Occupants} = 250(\overline{P})(H) \tag{10}$$

Other conversion factors or expressions are possible.

Electric Heating Gains

The operation of electric devices that deliver all heat that is generated into the interior of the building, for instance, lights, refrigerators, and the like, contribute to internal heating gain. Electric heating gains $Q^{Gains\text{-}Electric}$ (step 52) equal the amount of electricity used in the building that is converted to heat over the time period.

Care needs to be taken to ensure that the measured electricity consumption corresponds to the indoor usage. Two adjustments may be required. First, many electric utilities measure net electricity consumption. The energy produced by any photovoltaic (PV) system needs to be added back to net energy consumption (Net) to result in gross consumption if the building has a net-metered PV system. This amount can be estimated using time- and location-correlated solar resource data, as well as specific information about the orientation and other characteristics of the photovoltaic system, such as can be provided by the Solar Anywhere SystemCheck service (http://www.SolarAnywhere.com), a Web-based service operated by Clean Power Research, L.L.C., Napa, Calif., with the approach described, for instance, in commonly-assigned U.S. Patent application, entitled "Computer-Implemented System and Method for Estimating Gross Energy Load of a Building," Ser. No. 14/531,940, filed Nov. 3, 2014, pending, the disclosure of which is incorporated by reference, or measured directly.

Second, some uses of electricity may not contribute heat to the interior of the building and need be factored out as external electric heating gains (External). These uses include electricity used for electric vehicle charging, electric dryers (assuming that most of the hot exhaust air is vented outside of the building, as typically required by building code), outdoor pool pumps, and electric water heating using either direct heating or heat pump technologies (assuming that most of the hot water goes down the drain and outside the building—a large body of standing hot water, such as a bathtub filled with hot water, can be considered transient and not likely to appreciably increase the temperature indoors over the long run).

For instance, using a conversion factor from kWh to Btu of 3,412 Btu per kWh (since $Q^{Gains\text{-}Electric}$ is in units of Btu), internal electric gains $Q^{Gains\text{-}Electric}$ equal:

$$Q^{Gains\text{-}Electric} = (\overline{Net + PV - External})(H)\left(\frac{3{,}412\ Btu}{kWh}\right) \tag{11}$$

where Net represents net energy consumption, PV represents any energy produced by a PV system, External represents heating gains attributable to electric sources that do not contribute heat to the interior of a building. Other conversion factors or expressions are possible. The average delivered electricity $\overline{Net + PV - External}$ equals the total over the time period divided by the number of hours (H) in that time period.

$$\overline{Net + PV - External} = \frac{Net + PV - External}{H} \tag{12}$$

Solar Heating Gains

Solar energy that enters through windows, doors, and other openings in a building as sunlight will heat the interior. Solar heating gains $Q^{Gains\text{-}Solar}$ (step 53) equal the amount of heat delivered to a building from the sun. In the northern hemisphere, $Q^{Gains\text{-}Solar}$ can be estimated based on the south-facing window area ($m^2$) times the solar heating gain coefficient (SHGC) times a shading factor; together, these terms are represented by the effective window area (W). Solar heating gains $Q^{Gains\text{-}Solar}$ equal the product of W, the average direct vertical irradiance (DVI) available on a south-facing surface (Solar, as represented by DVI in $kW/m^2$), and the number of hours (H) in the time period. For instance, using a conversion factor from kWh to Btu of 3,412 Btu per kWh (since $Q^{Gains\text{-}Solar}$ is in units of Btu while average solar is in $kW/m^2$), solar heating gains $Q^{Gains\text{-}Solar}$ equal:

$$Q^{Gains\text{-}Solar} = (\overline{Solar})(W)(H)\left(\frac{3{,}412\ Btu}{kWh}\right) \tag{13}$$

Other conversion factors or expressions are possible.

Note that for reference purposes, the SHGC for one particular high quality window designed for solar gains, the Andersen High-Performance Low-E4 PassiveSun Glass window product, manufactured by Andersen Corporation, Bayport, Minn., is 0.54; many windows have SHGCs that are between 0.20 to 0.25.

Auxiliary Heating Gains

The internal sources of heating gain share the common characteristic of not being operated for the sole purpose of heating a building, yet nevertheless making some measureable contribution to the heat to the interior of a building. The fourth type of heating gain, auxiliary heating gains $Q^{Gains\text{-}Auxiliary\ Heating}$, consumes fuel specifically to provide heat to the building's interior and, as a result, must include conversion efficiency. The gains from auxiliary heating gains $Q^{Gains\text{-}Auxiliary\ Heating}$ (step 53) equal the product of the average hourly fuel consumed $\overline{Q}^{Fuel}$ times the hours (H) in the period times HVAC system efficiency $\eta^{HVAC}$.

$$Q^{Gains\text{-}Auxiliary\ Heating} = (\overline{Q}^{Fuel})(H)(\eta^{HVAC}) \tag{14}$$

Equation (14) can be stated in a more general form that can be applied to both heating and cooling seasons by adding a binary multiplier, HeatOrCool. The binary multiplier HeatOrCool equals 1 when the heating system is in operation and equals −1 when the cooling system is in operation. This more general form will be used in a subsequent section.

$$Q^{Gains(Losses)\text{-}HVAC} = (HeatOrCool)(\overline{Q}^{Fuel})(H)(\eta^{HVAC}) \tag{15}$$

Divide Thermal Conductivity into Parts

Consider the situation when the heating system is in operation. The HeatingOrCooling term in Equation (15) equals 1 in the heating season. As illustrated in FIG. 3, a building's thermal conductivity $UA^{Total}$, rather than being treated as a single value, can be conceptually divided into two parts (step 44), with a portion of $UA^{Total}$ allocated to "balance point thermal conductivity" ($UA^{Balance\ Point}$) and a portion to "auxiliary heating thermal conductivity" ($UA^{Auxiliary\ Heating}$), such as pictorially described supra with reference to FIG. 2. $UA^{Balance\ Point}$ corresponds to the heating losses that a building can sustain using only internal heating gains $Q^{Gains\text{-}Internal}$. This value is related to the concept that a building can sustain a specified balance point temperature in light of internal gains. However, instead of having a balance point temperature, some portion of the building $UA^{Balance\ Point}$ is considered to be thermally sustainable given heating gains from internal heating sources ($Q^{Gains\text{-}Internal}$). As the rest of the heating losses must be made up by auxiliary heating gains, the remaining portion of the building $UA^{Auxiliary\ Heating}$ is considered to be thermally sustainable given heating gains from auxiliary heating sources ($Q^{Gains\text{-}Auxiliary\ Heating}$). The amount of auxiliary heating gained is determined by the setting of the auxiliary heating source's thermostat or other control point. Thus, $UA^{Total}$ can be expressed as:

$$UA^{Total} = UA^{Balance\ Point} + UA^{Auxiliary\ Heating} \tag{16}$$

where $$UA^{Balance\ Point} = UA^{Occupants} + UA^{Electric} + UA^{Solar} \tag{17}$$

such that $UA^{Occupants}$, $UA^{Electric}$, and $UA^{Solar}$ respectively represent the thermal conductivity of internal heating sources, specifically, occupants, electric and solar.

In Equation (16), total thermal conductivity $UA^{Total}$ is fixed at a certain value for a building and is independent of weather conditions; $UA^{Total}$ depends upon the building's efficiency. The component parts of Equation (16), balance point thermal conductivity $UA^{Balance\ Point}$ and auxiliary heating thermal conductivity $UA^{Auxiliary\ Heating}$, however, are allowed to vary with weather conditions. For example, when the weather is warm, there may be no auxiliary heating in use and all of the thermal conductivity will be allocated to the balance point thermal conductivity $UA^{Balance\ Point}$ component.

Fuel consumption for heating losses $Q^{Losses}$ can be determined by substituting Equation (16) into Equation (7):

$$Q^{Losses} = (UA^{Balance\ Point} + UA^{Auxiliary\ Heating})(T^{Indoor} - T^{Outdoor})(H) \tag{18}$$

Balance Energy

Heating gains must equal heating losses for the system to balance (step 45), as further described infra with reference to FIG. 5. Heating energy balance is represented by setting Equation (8) equal to Equation (18):

$$Q^{Gains\text{-}Internal} + Q^{Gains\text{-}Auxiliary\ Heating} = (UA^{Balance\ Point} + UA^{Auxiliary\ Heating})(T^{Indoor} - T^{Outdoor})(H) \tag{19}$$

The result can then be divided by $(T^{Indoor} - T^{Outdoor})(H)$, assuming that this term is non-zero:

$$UA^{Balance\ Point} + UA^{Auxiliary\ Heating} = \frac{Q^{Gains\text{-}Internal} + Q^{Gains\text{-}Auxiliary\ Heating}}{(T^{Indoor} - T^{Outdoor})(H)} \tag{20}$$

Equation (20) expresses energy balance as a combination of both $UA^{Balance\ Point}$ and $UA^{Auxiliary\ Heating}$. FIG. 5 is a flow diagram showing a routine 60 for balancing energy for use in the method 40 of FIG. 3. Equation (20) can be further constrained by requiring that the corresponding terms on each side of the equation match, which will divide Equation (20) into a set of two equations:

$$UA^{Balance\ Point} = \frac{Q^{Gains\text{-}Internal}}{(T^{Indoor} - T^{Outdoor})(H)} \tag{21}$$

$$UA^{Auxiliary\ Heating} = \frac{Q^{Gains\text{-}Auxiliary\ Heating}}{(T^{Indoor} - T^{Outdoor})(H)} \tag{22}$$

The $UA^{Balance\ Point}$ should always be a positive value. Equation (21) accomplishes this goal in the heating season. An additional term, HeatOrCool is required for the cooling season that equals 1 in the heating season and −1 in the cooling season.

$$UA^{Balance\ Point} = \frac{(HeatOrCool)(Q^{Gains\text{-}Internal})}{(T^{Indoor} - T^{Outdoor})(H)} \tag{23}$$

HeatOrCool and its inverse are the same. Thus, internal gains equals:

$$Q^{Gains\text{-}Internal} = \frac{(HeatOrCool)(UA^{Balance\ Point})}{(T^{Indoor} - T^{Outdoor})(H)} \tag{24}$$

Components of $UA^{Balance\ Point}$

For clarity, $UA^{Balance\ Point}$ can be divided into three component values (step 61) by substituting Equation (9) into Equation (21):

$$UA^{Balance\ Point} = \frac{Q^{Gains\text{-}Occupants} + Q^{Gains\text{-}Electric} + Q^{Gains\text{-}Solar}}{(T^{Indoor} - T^{Outdoor})(H)} \tag{25}$$

Since $UA^{Balance\ Point}$ equals the sum of three component values (as specified in Equation (17)), Equation (25) can be mathematically limited by dividing Equation (25) into three equations:

$$UA^{Occupants} = \frac{Q^{Gains\text{-}Occupants}}{(T^{Indoor} - T^{Outdoor})(H)} \tag{26}$$

$$UA^{Electric} = \frac{Q^{Gains-Electric}}{(\overline{T}^{Indoor} - \overline{T}^{Outdoor})(H)} \quad (27)$$

$$UA^{Solar} = \frac{Q^{Gains-Solar}}{(\overline{T}^{Indoor} - \overline{T}^{Outdoor})(H)} \quad (28)$$

Solutions for Components of $UA^{Balance\ Point}$ and $UA^{Auxiliary\ Heating}$

The preceding equations can be combined to present a set of results with solutions provided for the four thermal conductivity components as follows. First, the portion of the balance point thermal conductivity associated with occupants $UA^{Occupants}$ (step 62) is calculated by substituting Equation (10) into Equation (26). Next, the portion of the balance point thermal conductivity $UA^{Electric}$ associated with internal electricity consumption (step 63) is calculated by substituting Equation (11) into Equation (27). Internal electricity consumption is the amount of electricity consumed internally in the building and excludes electricity consumed for HVAC operation, pool pump operation, electric water heating, electric vehicle charging, and so on, since these sources of electricity consumption result in heat or work being used external to the inside of the building. The portion of the balance point thermal conductivity $UA^{Solar}$ associated with solar gains (step 64) is then calculated by substituting Equation (13) into Equation (28). Finally, thermal conductivity $UA^{Auxiliary\ Heating}$ associated with auxiliary heating (step 64) is calculated by substituting Equation (14) into Equation (22).

$$UA^{Occupants} = \frac{250(\overline{P})}{(\overline{T}^{Indoor} - \overline{T}^{Outdoor})} \quad (29)$$

$$UA^{Electric} = \frac{(\overline{Net + PV - External})}{(\overline{T}^{Indoor} - \overline{T}^{Outdoor})}\left(\frac{3{,}412\ Btu}{kWh}\right) \quad (30)$$

$$UA^{Solar} = \frac{(\overline{Solar})(W)}{(\overline{T}^{Indoor} - \overline{T}^{Outdoor})}\left(\frac{3{,}412\ Btu}{kWh}\right) \quad (31)$$

$$UA^{Auxiliary\ Heating} = \frac{\overline{Q}^{Fuel}\eta^{HVAC}}{(\overline{T}^{Indoor} - \overline{T}^{Outdoor})} \quad (32)$$

Determine Fuel Consumption

Referring back to FIG. 3, Equation (32) can used to derive a solution to annual (or periodic) heating fuel consumption. First, Equation (16) is solved for $UA^{Auxiliary\ Heating}$.

$$UA^{Auxiliary\ Heating} = UA^{Total} - UA^{Balance\ Point} \quad (33)$$

Equation (33) is then substituted into Equation (32):

$$UA^{Total} - UA^{Balance\ Point} = \frac{\overline{Q}^{Fuel}\eta^{HVAC}}{(\overline{T}^{Indoor} - \overline{T}^{Outdoor})} \quad (34)$$

Finally, solving Equation (34) for fuel and multiplying by the number of hours (H) in (or duration of) the time period yields:

$$Q^{Fuel} = \frac{(UA^{Total} - UA^{Balance\ Point})(\overline{T}^{Indoor} - \overline{T}^{Outdoor})(H)}{\eta^{HVAC}} \quad (35)$$

Equation (35) is valid during the heating season and applies where $UA^{Total} \geq UA^{Balance\ Point}$. Otherwise, fuel consumption is 0.

Using Equation (35), annual (or periodic) heating fuel consumption $Q^{Fuel}$ can be determined (step 46). The building's thermal conductivity $UA^{Total}$, if already available through, for instance, the results of an energy audit, is obtained. Otherwise, $UA^{Total}$ can be determined by solving Equations (29) through (32) using historical fuel consumption data, such as shown, by way of example, in the table of FIG. 7, or by solving Equation (53), as further described infra. $UA^{Total}$ can also be empirically determined with the approach described, for instance, in commonly-assigned U.S. Patent application, entitled "System and Method for Empirically Estimating Overall Thermal Performance of a Building," Ser. No. 14/294,087, filed Jun. 2, 2014, pending, the disclosure of which is incorporated by reference. Other ways to determine $UA^{Total}$ are possible. $UA^{Balance\ Point}$ can be determined by solving Equation (25). The remaining values, average indoor temperature $\overline{T}^{Indoor}$ and average outdoor temperature $\overline{T}^{Outdoor}$, and HVAC system efficiency $\eta^{HVAC}$, can respectively be obtained from historical weather data and manufacturer specifications.

Practical Considerations

Equation (35) is empowering. Annual heating fuel consumption $Q^{Fuel}$ can be readily determined without encountering the complications of Equation (1), which is an equation that is difficult to solve due to the number and variety of unknown inputs that are required. The implications of Equation (35) in consumer decision-making, a general discussion, and sample applications of Equation (35) will now be covered.

Change in Fuel Requirements Associated with Decisions Available to Consumers

Figures 6, 7:
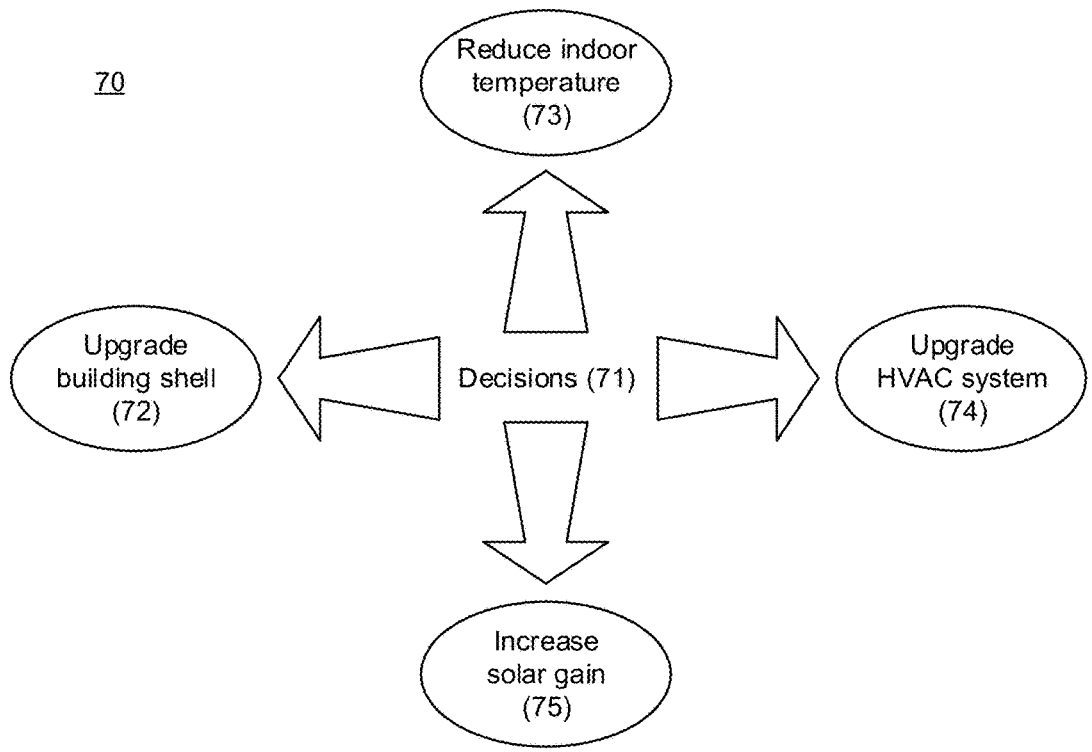
FIG. 6 is a process flow diagram showing, by way of example, consumer heating energy consumption-related decision points.
FIG. 7 is a table showing, by way of example, data used to calculate thermal conductivity.

Consumers have four decisions available to them that affects their energy consumption for heating. FIG. 6 is a process flow diagram showing, by way of example, consumer heating energy consumption-related decision points. These decisions 71 include:

1. Change the thermal conductivity $UA^{Total}$ by upgrading the building shell to be more thermally efficient (process 72).
2. Reduce or change the average indoor temperature by reducing the thermostat manually, programmatically, or through a "learning" thermostat (process 73).
3. Upgrade the HVAC system to increase efficiency (process 74).
4. Increase the solar gain by increasing the effective window area (process 75).

Other decisions are possible. Here, these four specific options can be evaluated supra by simply taking the derivative of Equation (35) with respect to a variable of interest. The result for each case is valid where $UA^{Total} \geq UA^{Balance\ Point}$. Otherwise, fuel consumption is 0.

Changes associated with other internal gains, such as increasing occupancy, increasing internal electric gains, or increasing solar heating gains, could be calculated using a similar approach.

Change in Thermal Conductivity

A change in thermal conductivity $UA^{Total}$ can affect a change in fuel requirements. The derivative of Equation (35) is taken with respect to thermal conductivity, which equals the average indoor minus outdoor temperatures times the number of hours divided by HVAC system efficiency. Note that initial thermal efficiency is irrelevant in the equation.

The effect of a change in thermal conductivity $UA^{Total}$ (process 72) can be evaluated by solving:

$$\frac{dQ^{Fuel}}{dUA^{Total}} = \frac{(\overline{T}^{Indoor} - \overline{T}^{Outdoor})(H)}{\eta^{HVAC}} \quad (36)$$

Change in Average Indoor Temperature

A change in average indoor temperature can also affect a change in fuel requirements. The derivative of Equation (35) is taken with respect to the average indoor temperature. Since $UA^{Balance\ Point}$ is also a function of average indoor temperature, application of the product rule is required. After simplifying, the effect of a change in average indoor temperature (process 73) can be evaluated by solving:

$$\frac{dQ^{Fuel}}{d\overline{T}^{Indoor}} = (UA^{Total})\left(\frac{H}{\eta^{HVAC}}\right) \quad (37)$$

Change in HVAC System Efficiency

As well, a change in HVAC system efficiency can affect a change in fuel requirements. The derivative of Equation (35) is taken with respect to HVAC system efficiency, which equals current fuel consumption divided by HVAC system efficiency. Note that this term is not linear with efficiency and thus is valid for small values of efficiency changes. The effect of a change in fuel requirements relative to the change in HVAC system efficiency (process 74) can be evaluated by solving:

$$\frac{dQ^{Fuel}}{d\eta^{HVAC}} = -Q^{Fuel}\left(\frac{1}{\eta^{HVAC}}\right) \quad (38)$$

Change in Solar Gains

An increase in solar gains can be accomplished by increasing the effective area of south-facing windows. Effective area can be increased by trimming trees blocking windows, removing screens, cleaning windows, replacing windows with ones that have higher SHGCs, installing additional windows, or taking similar actions. In this case, the variable of interest is the effective window area W. The total gain per square meter of additional effective window area equals the available resource (kWh/m$^2$) divided by HVAC system efficiency, converted to Btus. The derivative of Equation (35) is taken with respect to effective window area. The effect of an increase in solar gains (process 74) can be evaluated by solving:

$$\frac{dQ^{Fuel}}{d\overline{W}} = -\left[\frac{(\overline{Solar})(H)}{\eta^{HVAC}}\right]\left(\frac{3,412\ Btu}{kWh}\right) \quad (39)$$

Discussion

Both Equations (1) and (35) provide ways to calculate fuel consumption requirements. The two equations differ in several key ways:

1. $UA^{Total}$ only occurs in one place in Equation (35), whereas Equation (1) has multiple indirect and non-linear dependencies to $UA^{Total}$.
2. $UA^{Total}$ is divided into two parts in Equation (35), while there is only one occurrence of $UA^{Total}$ in Equation (1).
3. The concept of balance point thermal conductivity in Equation (35) replaces the concept of balance point temperature in Equation (1).
4. Heat from occupants, electricity consumption, and solar gains are grouped together in Equation (35) as internal heating gains, while these values are treated separately in Equation (1).

Second, Equations (29) through (32) provide empirical methods to determine both the point at which a building has no auxiliary heating requirements and the current thermal conductivity. Equation (1) typically requires a full detailed energy audit to obtain the data required to derive thermal conductivity. In contrast, Equations (25) through (28), as applied through the first approach, can substantially reduce the scope of an energy audit.

Third, both Equation (4) and Equation (36) provide ways to calculate a change in fuel requirements relative to a change in thermal conductivity. However, these two equations differ in several key ways:

1. Equation (4) is complex, while Equation (36) is simple.
2. Equation (4) depends upon current building thermal conductivity, balance point temperature, solar savings fraction, auxiliary heating efficiency, and a variety of other derivatives. Equation (36) only requires the auxiliary heating efficiency in terms of building-specific information.

Equation (36) implies that, as long as some fuel is required for auxiliary heating, a reasonable assumption, a change in fuel requirements will only depend upon average indoor temperature (as approximated by thermostat setting), average outdoor temperature, the number of hours (or other time units) in the (heating) season, and HVAC system efficiency. Consequently, any building shell (or envelope) investment can be treated as an independent investment. Importantly, Equation (36) does not require specific knowledge about building construction, age, occupancy, solar gains, internal electric gains, or the overall thermal conductivity of the building. Only the characteristics of the portion of the building that is being replaced, the efficiency of the HVAC system, the indoor temperature (as reflected by the thermostat setting), the outdoor temperature (based on location), and the length of the winter season are required; knowledge about the rest of the building is not required. This simplification is a powerful and useful result.

Fourth, Equation (37) provides an approach to assessing the impact of a change in indoor temperature, and thus the effect of making a change in thermostat setting. Note that Equation (31) only depends upon the overall efficiency of the building, that is, the building's total thermal conductivity $UA^{Total}$, the length of the winter season (in number of hours or other time units), and the HVAC system efficiency; Equation (31) does not depend upon either the indoor or outdoor temperature.

Equation (31) is useful in assessing claims that are made by HVAC management devices, such as the Nest thermostat device, manufactured by Nest Labs, Inc., Palo Alto, Calif., or the Lyric thermostat device, manufactured by Honeywell Int'l Inc., Morristown, N.J., or other so-called "smart" thermostat devices. The fundamental idea behind these types of HVAC management devices is to learn behavioral patterns, so that consumers can effectively lower (or raise) their average indoor temperatures in the winter (or summer) months without affecting their personal comfort. Here, Equation (31) could be used to estimate the value of heating and cooling savings, as well as to verify the consumer behaviors implied by the new temperature settings.

Balance Point Temperature

Before leaving this section, balance point temperature should briefly be discussed. The formulation in this first approach does not involve balance point temperature as an input. A balance point temperature, however, can be calculated to equal the point at which there is no fuel consumption, such that there are no gains associated with auxiliary heating ($Q^{Gains\text{-}Auxiliary\ Heating}$ equals 0) and the auxiliary heating thermal conductivity ($UA^{Auxiliary\ Heating}$ in Equation (32)) is zero. Inserting these assumptions into Equation (20) and labeling $T^{Outdoor}$ as $T^{Balance\ Point}$ yields:

$$Q^{Gains\text{-}Internal} = UA^{Total}(T^{Indoor} - T^{Balance\ Point})(H) \qquad (40)$$

Equation (40) simplifies to:

$$\overline{T}^{Balance\ Point} = \overline{T}^{Indoor} - \frac{\overline{Q}^{Gains\text{-}Internal}}{UA^{Total}} \qquad (41)$$

where $$\overline{Q}^{Gains\text{-}Internal} = \frac{Q^{Gains\text{-}Internal}}{H}$$

Equation (41) is identical to Equation (2), except that average values are used for indoor temperature $\overline{T}^{Indoor}$, balance point temperature $\overline{T}^{Balance\ Point}$, and fuel consumption for internal heating gains $Q^{Gains\text{-}Internal}$ and that heating gains from occupancy (Q Gains-Occupants), electric ($Q^{Gains\text{-}Electric}$), and solar ($Q^{Gains\text{-}Solar}$) are all included as part of internal heating gains ($Q^{Gains\text{-}Internal}$).

Application: Change in Thermal Conductivity Associated with One Investment

An approach to calculating a new value for total thermal conductivity $\widehat{UA}^{Total}$ after a series of M changes (or investments) are made to a building is described in commonly-assigned U.S. Patent application, entitled "System and Method for Interactively Evaluating Personal Energy-Related Investments," Ser. No. 14/294,079, filed Jun. 2, 2014, pending, the disclosure of which is incorporated by reference. The approach is summarized therein in Equation (41), which provides:

$$\widehat{UA}^{Total} = UA^{Total} + \sum_{j=1}^{M}(U^j - \hat{U}^j)A^j + \rho c(n - \hat{n})V \qquad (42)$$

where a caret symbol (^) denotes a new value, infiltration losses are based on the density of air ($\rho$), specific heat of air (c), number of air changes per hour (n), and volume of air per air change (V). In addition, $U^j$ and $\hat{U}^j$ respectively represent the existing and proposed U-values of surface j, and $A^j$ represents the surface area of surface j. The volume of the building V can be approximated by multiplying building square footage by average ceiling height. The equation, with a slight restatement, equals:

$$\widehat{UA}^{Total} = UA^{Total} + \Delta UA^{Total} \qquad (43)$$

and $$\Delta UA^{Total} = \sum_{j=1}^{M}(U^j - \hat{U}^j)A^j + \rho c(n - \hat{n})V \qquad (44)$$

If there is only one investment, the m superscripts can be dropped and the change in thermal conductivity $UA^{Total}$ equals the area (A) times the difference of the inverse of the old and new R-values R and $\hat{R}$:

$$\Delta UA^{Total} = A(U - \hat{U}) = A\left(\frac{1}{R} - \frac{1}{\hat{R}}\right). \qquad (45)$$

Fuel Savings

The fuel savings associated with a change in thermal conductivity $UA^{Total}$ for a single investment equals Equation (45) times (36):

$$\Delta Q^{Fuel} = \Delta UA^{Total}\frac{dQ^{Fuel}}{dUA^{Total}} = A\left(\frac{1}{R} - \frac{1}{\hat{R}}\right)\frac{(\overline{T}^{Indoor} - \overline{T}^{Outdoor})(H)}{\eta^{HVAC}} \qquad (46)$$

where $\Delta Q^{Fuel}$ signifies the change in fuel consumption.

Economic Value

The economic value of the fuel savings (Annual Savings) equals the fuel savings times the average fuel price (Price) for the building in question:

$$\text{Annual Savings} = A\left(\frac{1}{R} - \frac{1}{\hat{R}}\right)\frac{(\overline{T}^{Indoor} - \overline{T}^{Outdoor})(H)}{\eta^{HVAC}}(\text{Price}) \qquad (47)$$

where $$\text{Price} = \begin{cases} \dfrac{\text{Price}^{NG}}{10^5} & \text{if price has units of \$ per therm} \\ \dfrac{\text{Price}^{Electricity}}{3,412} & \text{if price has units of \$ per kWh} \end{cases}$$

where $\text{Price}^{NG}$ represents the price of natural gas and $\text{Price}^{Electricity}$ represents the price of electricity. Other pricing amounts, pricing conversion factors, or pricing expressions are possible.

Example

Consider an example. A consumer in Napa, Calif. wants to calculate the annual savings associating with replacing a 20 ft² single-pane window that has an R-value of 1 with a high efficiency window that has an R-value of 4. The average temperature in Napa over the 183-day winter period (4,392 hours) from October 1 to March 31 is 50° F. The consumer sets his thermostat at 68° F., has a 60 percent efficient natural gas heating system, and pays $1 per therm for natural gas. How much money will the consumer save per year by making this change?

Putting this information into Equation (47) suggests that he will save $20 per year:

$$\text{Annual Savings} = 20\left(\frac{1}{1} - \frac{1}{4}\right)\frac{(60 - 50)(4,392)}{0.6}\left(\frac{1}{10^5}\right) = \$20 \qquad (48)$$

Application: Validate Building Shell Improvements Savings

Many energy efficiency programs operated by power utilities grapple with the issue of measurement and evaluation (M&E), particularly with respect to determining whether savings have occurred after building shell improvements were made. Equations (29) through (32) can be applied to help address this issue. These equations can be used to calculate a building's total thermal conductivity $UA^{Total}$. This result provides an empirical approach to validating the benefits of building shell investments using measured data.

Equations (29) through (32) require the following inputs:
1) Weather:
   a) Average outdoor temperature (° F.).
   b) Average indoor temperature (° F.).
   c) Average direct solar resource on a vertical, south-facing surface.
2) Fuel and energy:
   a) Average gross indoor electricity consumption.
   b) Average natural gas fuel consumption for space heating.
   c) Average electric fuel consumption for space heating.
3) Other inputs:
   a) Average number of occupants.
   b) Effective window area.
   c) HVAC system efficiency.

Weather data can be determined as follows. Indoor temperature can be assumed based on the setting of the thermostat (assuming that the thermostat's setting remained constant throughout the time period), or measured and recorded using a device that takes hourly or periodic indoor temperature measurements, such as a Nest thermostat device or a Lyric thermostat device, cited supra, or other so-called "smart" thermostat devices. Outdoor temperature and solar resource data can be obtained from a service, such as Solar Anywhere SystemCheck, cited supra, or the National Weather Service. Other sources of weather data are possible.

Fuel and energy data can be determined as follows. Monthly utility billing records provide natural gas consumption and net electricity data. Gross indoor electricity consumption can be calculated by adding PV production, whether simulated using, for instance, the Solar Anywhere SystemCheck service, cited supra, or measured directly, and subtracting out external electricity consumption, that is, electricity consumption for electric devices that do not deliver all heat that is generated into the interior of the building. External electricity consumption includes electric vehicle (EV) charging and electric water heating. Other types of external electricity consumption are possible. Natural gas consumption for heating purposes can be estimated by subtracting non-space heating consumption, which can be estimated, for instance, by examining summer time consumption using an approach described in commonly-assigned U.S. Patent application, entitled "System and Method for Facilitating Implementation of Holistic Zero Net Energy Consumption," Ser. No. 14/531,933, filed Nov. 3, 2014, pending, the disclosure of which is incorporated by reference. Other sources of fuel and energy data are possible.

Finally, the other inputs can be determined as follows. The average number of occupants can be estimated by the building owner or occupant. Effective window area can be estimated by multiplying actual south-facing window area times solar heat gain coefficient (estimated or based on empirical tests, as further described infra), and HVAC system efficiency can be estimated (by multiplying reported furnace rating times either estimated or actual duct system efficiency), or can be based on empirical tests, as further described infra. Other sources of data for the other inputs are possible.

Consider an example. FIG. 7 is a table 80 showing, by way of example, data used to calculate thermal conductivity. The data inputs are for a sample house in Napa, Calif. based on the winter period of October 1 to March 31 for six winter seasons, plus results for a seventh winter season after many building shell investments were made. (Note the building improvements facilitated a substantial increase in the average indoor temperature by preventing a major drop in temperature during night-time and non-occupied hours.) South-facing windows had an effective area of 10 m² and the solar heat gain coefficient is estimated to be 0.25 for an effective window area of 2.5 m². The measured HVAC system efficiency of 59 percent was based on a reported furnace efficiency of 80 percent and an energy audit-based duct efficiency of 74 percent.

Figures 8, 9:
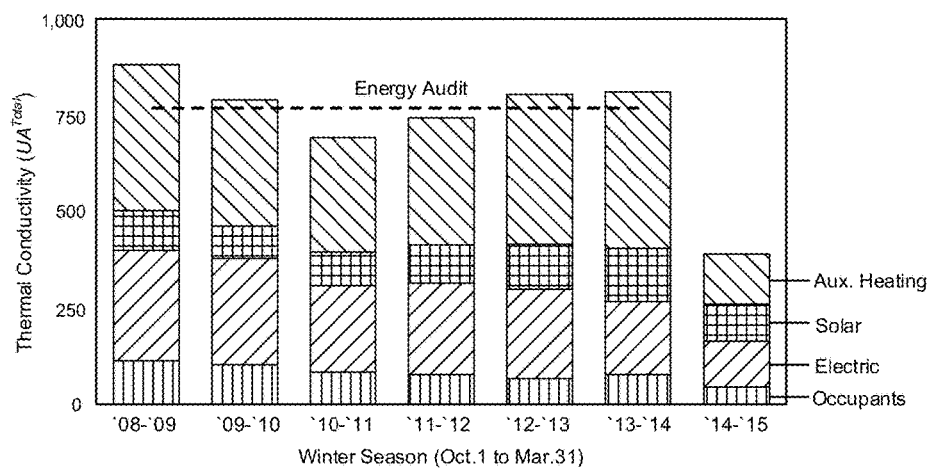
FIG. 8 is a table showing, by way of example, thermal conductivity results for each season using the data in the table of FIG. 7 as inputs into Equations (29) through (32).
FIG. 9 is a graph showing, by way of example, a plot of the thermal conductivity results in the table of FIG. 8.

FIG. 8 is a table 90 showing, by way of example, thermal conductivity results for each season using the data in the table 80 of FIG. 7 as inputs into Equations (29) through (32). Thermal conductivity is in units of Btu/h-° F. FIG. 9 is a graph 100 showing, by way of example, a plot of the thermal conductivity results in the table 90 of FIG. 8. The x-axis represents winter seasons for successive years, each winter season running from October 1 to March 31. The y-axis represents thermal conductivity. The results from a detailed energy audit, performed in early 2014, are superimposed on the graph. The energy audit determined that the house had a thermal conductivity of 773 Btu/h-° F. The average result estimated for the first six seasons was 791 Btu/h-° F. A major amount of building shell work was performed after the 2013-2014 winter season, and the results show a 50-percent reduction in heating energy consumption in the 2014-2015 winter season.

Application: Evaluate Investment Alternatives

Figure 10:
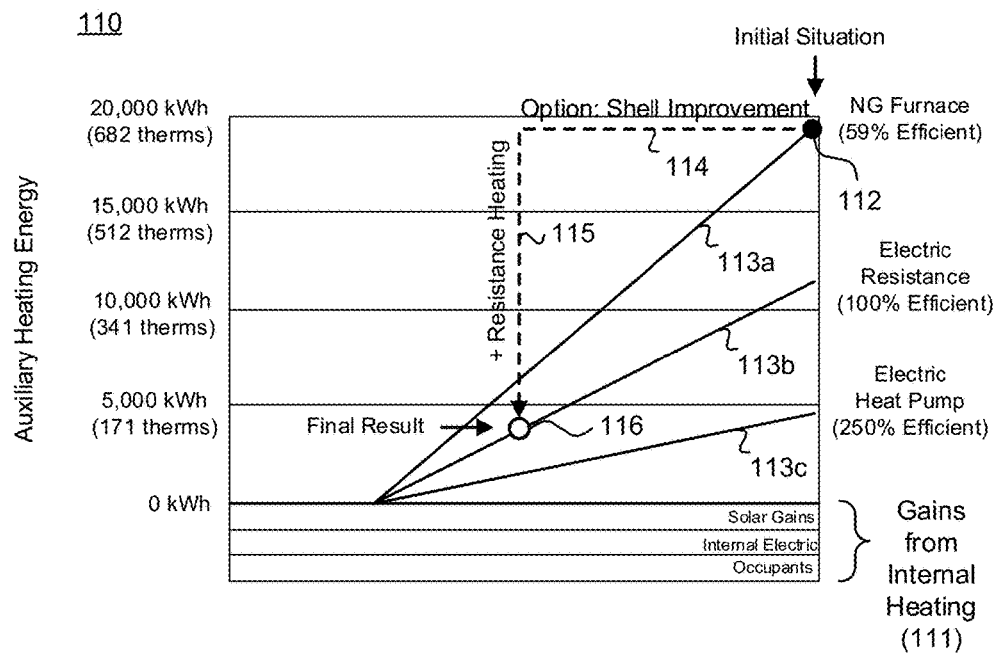
FIG. 10 is a graph showing, by way of example, an auxiliary heating energy analysis and energy consumption investment options.

The results of this work can be used to evaluate potential investment alternatives. FIG. 10 is a graph 110 showing, by way of example, an auxiliary heating energy analysis and energy consumption investment options. The x-axis represents total thermal conductivity, $UA^{Total}$ in units of Btu/hr-° F. The y-axis represents total heating energy. The graph presents the analysis of the Napa, Calif. building from the earlier example, supra, using the equations previously discussed. The three lowest horizontal bands correspond to the heat provided through internal gains 111, including occupants, heat produced by operating electric devices, and solar heating. The solid circle 112 represents the initial situation with respect to heating energy consumption. The diagonal lines 113a, 113b, 113c represent three alternative heating system efficiencies versus thermal conductivity (shown in the graph as building losses). The horizontal dashed line 114 represents an option to improve the building shell and the vertical dashed line 115 represents an option to switch to electric resistance heating. The plain circle 116 represents the final situation with respect to heating energy consumption.

Other energy consumption investment options (not depicted) are possible. These options include switching to an electric heat pump, increasing solar gain through window replacement or tree trimming (this option would increase the height of the area in the graph labeled "Solar Gains"), or lowering the thermostat setting. These options can be compared using the approach described with reference to Equations (25) through (28) to compare the options in terms of their costs and savings, which will help the homeowner to make a wiser investment.

Second Approach: Time Series Fuel Consumption

The previous section presented an annual fuel consumption model. This section presents a detailed time series model. This section also compares results from the two methods and provides an example of how to apply the on-site empirical tests.

Building-Specific Parameters

Figure 11:
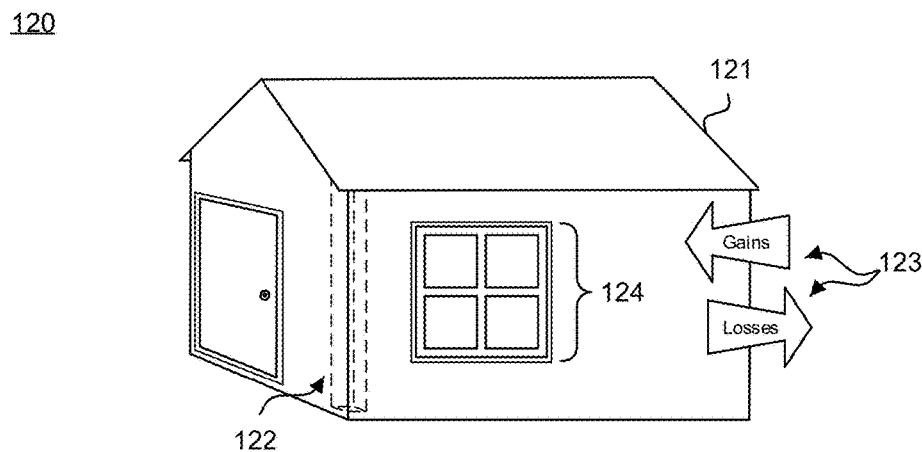
FIG. 11 is a functional block diagram showing heating losses and gains relative to a structure.

The building temperature model used in this second approach requires three building parameters: (1) thermal mass; (2) thermal conductivity; and (3) effective window area. FIG. 11 is a functional block diagram showing thermal mass, thermal conductivity, and effective window area relative to a structure 121. By way of introduction, these parameters will now be discussed.

Thermal Mass (M)

The heat capacity of an object equals the ratio of the amount of heat energy transferred to the object and the resulting change in the object's temperature. Heat capacity is also known as "thermal capacitance" or "thermal mass" (122) when used in reference to a building. Thermal mass Q is a property of the mass of a building that enables the building to store heat, thereby providing "inertia" against temperature fluctuations. A building gains thermal mass through the use of building materials with high specific heat capacity and high density, such as concrete, brick, and stone.

The heat capacity is assumed to be constant when the temperature range is sufficiently small. Mathematically, this relationship can be expressed as:

$$Q_{\Delta t} = M(T_{t+\Delta t}^{Indoor} - T_t^{Indoor}) \tag{49}$$

where M equals the thermal mass of the building and temperature units T are in °F. Q is typically expressed in Btu or Joules. In that case, M has units of Btu/°F. Q can also be divided by 1 kWh/3,412 Btu to convert to units of kWh/°F.

Thermal Conductivity ($UA^{Total}$)

The building's thermal conductivity $UA^{Total}$ (123) is the amount of heat that the building gains or losses as a result of conduction and infiltration. Thermal conductivity $UA^{Total}$ was discussed supra with reference to the first approach for modeling annual heating fuel consumption.

Effective Window Area (W)

The effective window area (in units of m²) (124), also discussed in detail supra, specifies how much of an available solar resource is absorbed by the building. Effective window area is the dominant means of solar gain in a typical building during the winter and includes the effect of physical shading, window orientation, and the window's solar heat gain coefficient. In the northern hemisphere, the effective window area is multiplied by the available average direct irradiance on a vertical, south-facing surface (kW/m²), times the amount of time (H) to result in the kWh obtained from the windows.

Energy Gain or Loss

The amount of heat transferred to or extracted from a building (Q) over a time period of Δt is based on a number of factors, including:

1) Loss (or gain if outdoor temperature exceeds indoor temperature) due to conduction and infiltration and the differential between the indoor and outdoor temperatures.
2) Gain, when the HVAC system is in the heating mode, or loss, when the HVAC system is in the cooling mode.
3) Gain associated with:
   a) Occupancy and heat given off by people.
   b) Heat produced by consuming electricity inside the building.
   c) Solar radiation.

Mathematically, Q can be expressed as:

$$Q_{\Delta t} = \left[ \underbrace{UA^{Total}(\overline{T}^{Outdoor} - \overline{T}^{Indoor})}_{\text{Envelope Gain or Loss}} + \underbrace{(250)\overline{P}}_{\text{Occupancy Gain}} + \underbrace{\overline{Electric}\left(\frac{3{,}412 \text{ Btu}}{1 \text{ kWh}}\right)}_{\text{Internal Electric Gain}} + \right.$$

$$\left. \underbrace{\overline{WSolar}\left(\frac{3{,}412 \text{ Btu}}{1 \text{ kWh}}\right)}_{\text{Solar Gain}} + \underbrace{(HeatOrCool)R^{HVAC}\eta^{HVAC}\overline{Status}}_{\text{HVAC Gain or Loss}} \right] \Delta t$$

where:

Except as noted otherwise, the bars over the variable names represent the average value over Δt hours, that is, the duration of the applicable empirical test. For instance, $T^{Outdoor}$ represents the average outdoor temperature between the time interval of t and t+Δt.

$UA^{Total}$ is the thermal conductivity (in units of Btu/hour-°F.).

W is the effective window area (in units of m²).

Occupancy Gain is based on the average number of people ($\overline{P}$) in the building during the applicable empirical test (and the heat produced by those people). The average person is assumed to produce 250 Btu/hour.

Internal Electric Gain is based on heat produced by indoor electricity consumption ($\overline{Electric}$), as averaged over the applicable empirical test, but excludes electricity for purposes that do not produce heat inside the building, for instance, electric hot water heating where the hot water is discarded down the drain, or where there is no heat produced inside the building, such as is the case with EV charging.

Solar Gain is based on the average available normalized solar irradiance ($\overline{Solar}$) during the applicable empirical test (with units of kW/m²). This value is the irradiance on a vertical surface to estimate solar received on windows; global horizontal irradiance (GHI) can be used as a proxy for this number when W is allowed to change on a monthly basis.

HVAC Gain or Loss is based on whether the HVAC is in heating or cooling mode (GainOrLoss is 1 for heating and −1 for cooling), the rating of the HVAC system (R in Btu), HVAC system efficiency ($\eta^{HVAC}$, including both conversion and delivery system efficiency), average operation status ($\overline{Status}$) during the empirical test, a time series value that is either off (0 percent) or on (100 percent), Other conversion factors or expressions are possible.

Energy Balance

Equation (49) reflects the change in energy over a time period and equals the product of the temperature change and the building's thermal mass. Equation (50) reflects the net gain in energy over a time period associated with the various component sources. Equation (49) can be set to equal Equation (50), since the results of both equations equal the same quantity and have the same units (Btu). Thus, the total heat change of a building will equal the sum of the individual heat gain/loss components:

$$\underbrace{M(T_{t+\Delta t}^{Indoor} - T_t^{Indoor})}_{\text{Total Heat Change}} = \left[ \underbrace{UA^{Total}(\overline{T}^{Outdoor} - \overline{T}^{Indoor})}_{\text{Envelop Gain or Loss}} + \right. \tag{51}$$

$$\underbrace{(250)\overline{P}}_{\text{Occupancy Gain}} + \underbrace{\overline{Electric}\left(\frac{3{,}412 \text{ Btu}}{1 \text{ kWh}}\right)}_{\text{Internal Electic Gain}} +$$

-continued $$W \overline{Solar} \left( \frac{3,412 \text{ Btu}}{1 \text{ kWh}} \right) + \overline{(HeatOrCool)R^{HVAC}\eta^{HVAC}\overline{Status}} \Bigg] \Delta t$$

Figures 12, 13:
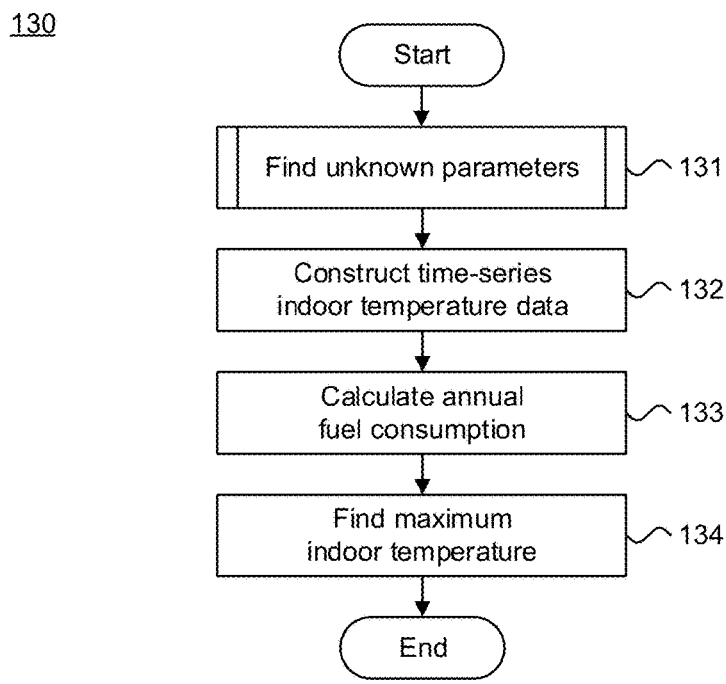
FIG. 12 is a flow diagram showing a computer-implemented method for modeling interval building heating energy consumption in accordance with a further embodiment.
FIG. 13 is a table showing the characteristics of empirical tests used to solve for the four unknown parameters in Equation (51).

Equation (51) can be used for several purposes. FIG. 12 is a flow diagram showing a computer-implemented method 130 for modeling interval building heating energy consumption in accordance with a further embodiment. Execution of the software can be performed with the assistance of a computer system, such as further described infra with reference to FIG. 29, as a series of process or method modules or steps.

As a single equation, Equation (51) is potentially very useful, despite having five unknown parameters. In this second approach, the unknown parameters are solved by performing a series of short duration empirical tests (step 131), as further described infra with reference to FIG. 14. Once the values of the unknown parameters are found, a time series of indoor temperature data can be constructed (step 132), which will then allow annual fuel consumption to be calculated (step 133) and maximum indoor temperature to be found (step 134). The short duration tests will first be discussed.

Empirically Determining Building- and Equipment-Specific Parameters Using Short Duration Tests A series of tests can be used to iteratively solve Equation (51) to obtain the values of the unknown parameters by ensuring that the portions of Equation (51) with the unknown parameters are equal to zero. These tests are assumed to be performed when the HVAC is in heating mode for purposes of illustration. Other assumptions are possible.

FIG. 13 is a table 140 showing the characteristics of empirical tests used to solve for the five unknown parameters in Equation (51). The empirical test characteristics are used in a series of sequentially-performed short duration tests; each test builds on the findings of earlier tests to replace unknown parameters with found values.

Figure 14:
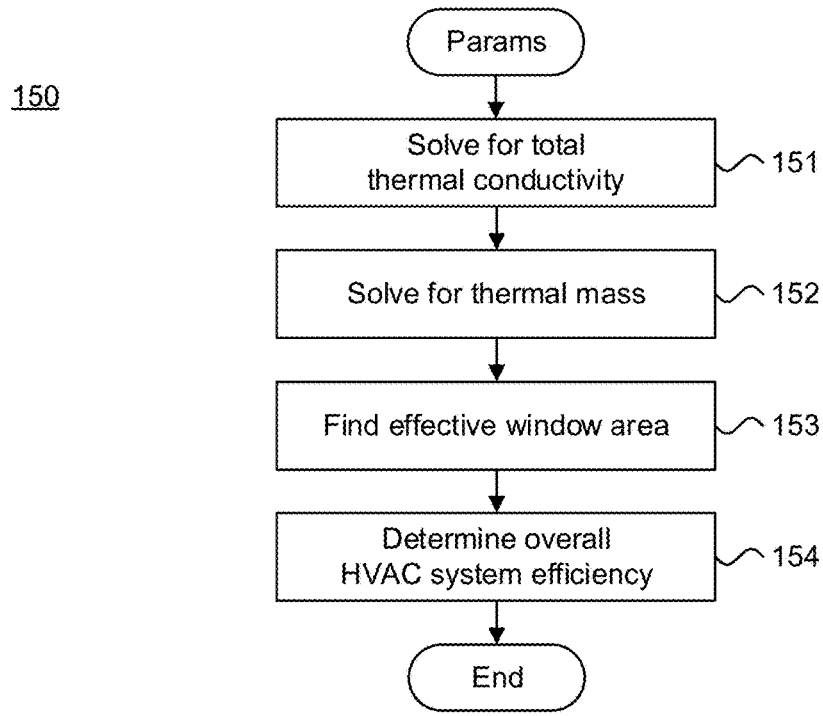
FIG. 14 is a flow diagram showing a routine for empirically determining building- and equipment-specific parameters using short duration tests for use in the method of FIG. 12.

The empirical tests require the use of several components, including a control for turning an HVAC system ON or OFF, depending upon the test; an electric controllable interior heat source; a monitor to measure the indoor temperature during the test; a monitor to measure the outdoor temperature during the test; and a computer or other computational device to assemble the test results and finding thermal conductivity, thermal mass, effective window area, and HVAC system efficiency of a building based on the findings. The components can be separate units, or could be consolidated within one or more combined units. For instance, a computer equipped with temperature probes could both monitor, record and evaluate temperature findings. FIG. 14 is a flow diagram showing a routine 150 for empirically determining building- and equipment-specific parameters using short duration tests for use in the method 130 of FIG. 12. The approach is to run a serialized series of empirical tests. The first test solves for the building's total thermal conductivity ($UA^{Total}$) (step 151). The second test uses the empirically-derived value for $UA^{Total}$ to solve for the building's thermal mass (M) (step 152). The third test uses both of these results, thermal conductivity and thermal mass, to find the building's effective window area (W) (step 153). Finally, the fourth test uses the previous three test results to determine the overall HVAC system efficiency (step 145). Consider how to perform each of these tests.

Test 1: Building Thermal Conductivity ($UA^{Total}$)

The first step is to find the building's total thermal conductivity ($UA^{Total}$) (step 151). Referring back to the table in FIG. 13, this short-duration test occurs at night (to avoid any solar gain) with the HVAC system off (to avoid any gain from the HVAC system), and by having the indoor temperature the same at the beginning and the ending of the test by operating an electric controllable interior heat source, such as portable electric space heaters that operate at 100% efficiency, so that there is no change in the building temperature's at the beginning and at the ending of the test. Thus, the interior heart source must have sufficient heating capacity to maintain the building's temperature state. Ideally, the indoor temperature would also remain constant to avoid any potential concerns with thermal time lags.

These assumptions are input into Equation (51):

$$M(0) = \left[ UA^{Total}(\overline{T}^{Outdoor} - \overline{T}^{Outdoor}) + \right. \quad (52)$$

$$(250)\overline{P} + \overline{Electric}\left(\frac{3,412 \text{ Btu}}{1 \text{ kWh}}\right) +$$

$$\left. W(0)\left(\frac{3,412 \text{ Btu}}{1 \text{ kWh}}\right) + (1)R^{HVAC}\eta^{HVAC}(0) \right] \Delta t$$

The portions of Equation (52) that contain four of the five unknown parameters now reduce to zero. The result can be solved for $UA^{Total}$:

$$UA^{Total} = \frac{\left[(250)\overline{P} + \overline{Electric}\left(\frac{3,412 \text{ Btu}}{1 \text{ kWh}}\right)\right]}{(\overline{T}^{Outdoor} - \overline{T}^{Outdoor})} \quad (53)$$

where $\overline{T}^{Indoor}$ represents the average indoor temperature during the empirical test, $\overline{T}^{Outdoor}$ represents the average outdoor temperature during the empirical test, $\overline{P}$ represents the average number of occupants during the empirical test, and $\overline{Electric}$ represents average indoor electricity consumption during the empirical test.

Equation (53) implies that the building's thermal conductivity can be determined from this test based on average number of occupants, average power consumption, average indoor temperature, and average outdoor temperature.

Test 2: Building Thermal Mass (M) The second step is to find the building's thermal mass (M) (step 152). This step is accomplished by constructing a test that guarantees M is specifically non-zero since $UA^{Total}$ is known based on the results of the first test. This second test is also run at night, so that there is no solar gain, which also guarantees that the starting and the ending indoor temperatures are not the same, that is, $T_{t+\Delta t}^{Indoor} \neq T_t^{Indoor}$, respectively at the outset and conclusion of the test by not operating the HVAC system. These assumptions are input into Equation (51) and solving yields a solution for M:

$$M = \frac{\left[ UA^{Total}(\overline{T}^{Outdoor} - \overline{T}^{Outdoor}) + (250)\overline{P} + \overline{Electric}\left(\frac{3,412 \text{ Btu}}{1 \text{ kWh}}\right) \right]}{(T_{t+\Delta t}^{Indoor} - T_t^{Indoor})} \Delta t \quad (54)$$

where $UA^{Total}$ represents the thermal conductivity, $\overline{T^{Indoor}}$ represents the average indoor temperature during the empirical test, $\overline{T^{Outdoor}}$ represents the average outdoor temperature during the empirical test, $\overline{P}$ represents the average number of occupants during the empirical test, $\overline{Electric}$ represents average indoor electricity consumption during the empirical test, t represents the time at the beginning of the empirical test, $\Delta t$ represents the duration of the empirical test, $T_{t+\Delta t}^{Indoor}$ represents the ending indoor temperature, $T_t^{Indoor}$ represents the starting indoor temperature, and $T_{t+\Delta t}^{Indoor} \neq T_t^{Indoor}$.

Test 3: Building Effective Window Area (W)

The third step to find the building's effective window area (W) (step 153) requires constructing a test that guarantees that solar gain is non-zero. This test is performed during the day with the HVAC system turned off. Solving for W yields:

$$W = \left\{ \left[ \frac{M(T_{t+\Delta t}^{Indoor} - T_t^{Indoor})}{3{,}412 \Delta t} \right] - \frac{UA^{Total}(\overline{T^{Outdoor}} - \overline{T^{Indoor}})}{3{,}412} - \frac{(250)\overline{P}}{3{,}412} - \overline{Electric} \right\} \left[ \frac{1}{\overline{Solar}} \right]$$

where M represents the thermal mass, t represents the time at the beginning of the empirical test, $\Delta t$ represents the duration of the empirical test, $T_{t+\Delta t}^{Indoor}$ represents the ending indoor temperature, and $T_t^{Indoor}$ represents the starting indoor temperature, $UA^{Total}$ represents the thermal conductivity, $\overline{T^{Indoor}}$ represents the average indoor temperature, $\overline{T^{Outdoor}}$ represents the average outdoor temperature, $\overline{P}$ represents the average number of occupants during the empirical test, $\overline{Electric}$ represents average electricity consumption during the empirical test, and $\overline{Solar}$ represents the average solar energy produced during the empirical test.

Test 4: HVAC System Efficiency ($\eta^{Furnace}\eta^{Delivery}$)

The fourth step determines the HVAC system efficiency (step 154). Total HVAC system efficiency is the product of the furnace efficiency and the efficiency of the delivery system, that is, the duct work and heat distribution system. While these two terms are often solved separately, the product of the two terms is most relevant to building temperature modeling. This test is best performed at night, so as to eliminate solar gain. Thus:

$$\eta^{HVAC} = \left[ \frac{M(T_{t+\Delta t}^{Indoor} - T_t^{Indoor})}{\Delta t} - UA^{Total}(\overline{T^{Outdoor}} - \overline{T^{Indoor}}) - (250)\overline{P} - \overline{Electric}\left(\frac{3{,}412 \text{ Btu}}{1 \text{ kWh}}\right)\right]\left[\frac{1}{(1)R^{HVAC}\overline{Status}}\right] \quad (56)$$

where M represents the thermal mass, t represents the time at the beginning of the empirical test, $\Delta t$ represents the duration of the empirical test, $T_{t+\Delta t}^{Indoor}$ represents the ending indoor temperature, and $T_t^{Indoor}$ represents the starting indoor temperature, $UA^{Total}$ represents the thermal conductivity, $\overline{T^{Indoor}}$ represents the average indoor temperature, $\overline{T^{Outdoor}}$ represents the average outdoor temperature, $\overline{P}$ represents the average number of occupants during the empirical test, $\overline{Electric}$ represents average electricity consumption during the empirical test, $\overline{Status}$ represents the average furnace operation status, and $R^{Furnace}$ represents the rating of the furnace.

Note that HVAC duct efficiency can be determined without performing a duct leakage test if the generation efficiency of the furnace is known. This observation usefully provides an empirical method to measure duct efficiency without having to perform a duct leakage test.

Time Series Indoor Temperature Data

The previous subsection described how to perform a series of empirical short duration tests to determine the unknown parameters in Equation (51). Commonly-assigned U.S. patent application Ser. No. 14/531,933, cited supra, describes how a building's $UA^{Total}$ can be combined with historical fuel consumption data to estimate the benefit of improvements to a building. While useful, estimating the benefit requires measured time series fuel consumption and HVAC system efficiency data. Equation (51), though, can be used to perform the same analysis without the need for historical fuel consumption data.

Referring back to FIG. 12, Equation (51) can be used to construct time series indoor temperature data (step 132) by making an approximation. Let the time period ($\Delta t$) be short (an hour or less), so that the average values are approximately equal to the value at the beginning of the time period, that is, assume $\overline{T^{Outdoor}} \neq T_t^{Outdoor}$. The average values in Equation (51) can be replaced with time-specific subscripted values and solved to yield the final indoor temperature.

$$T_{t+\Delta t}^{Indoor} = T_t^{Indoor} + \left[\frac{1}{M}\right]\Bigg[UA^{Total}(T_t^{Outdoor} - T_t^{Indoor}) + (250)P_t + Electric_t\left(\frac{3{,}412 \text{ Btu}}{1 \text{ kWh}}\right) + WSolar_t\left(\frac{3{,}412 \text{ Btu}}{1 \text{ kWh}}\right) + (HeatOrCool)R^{HVAC}\eta^{HVAC}Status_t\Bigg]\Delta t \quad (57)$$

Once $T_{t+\Delta t}^{Indoor}$ is known, Equation (57) can be used to solve for $T_{t+2\Delta t}^{Indoor}$ and so on.

Importantly, Equation (57) can be used to iteratively construct indoor building temperature time series data with no specific information about the building's construction, age, configuration, number of stories, and so forth. Equation (57) only requires general weather datasets (outdoor temperature and irradiance) and building-specific parameters. The control variable in Equation (57) is the fuel required to deliver the auxiliary heat at time t, as represented in the Status variable, that is, at each time increment, a decision is made whether to run the HVAC system.

Seasonal Fuel Consumption

Equation (51) can also be used to calculate seasonal fuel consumption (step 133) by letting $\Delta t$ equal the number of hours (H) in the entire season, either heating or cooling (and not the duration of the applicable empirical test), rather than making $\Delta t$ very short (such as an hour, as used in an applicable empirical test). The indoor temperature at the start and the end of the season can be assumed to be the same or, alternatively, the total heat change term on the left side of the equation can be assumed to be very small and set equal to zero. Rearranging Equation (51) provides:

$$(HeatOrCool)R^{HVAC}\eta^{HVAC}\overline{Status}(H) = -[UA^{Total}(\overline{T^{Outdoor}} - \overline{T^{Indoor}})](H) - \left[(250)\overline{P} + \overline{Electric}\left(\frac{3{,}412 \text{ Btu}}{1 \text{ kWh}}\right) + W\overline{Solar}\left(\frac{3{,}412 \text{ Btu}}{1 \text{ kWh}}\right)\right](H) \quad (58)$$

Total seasonal fuel consumption based on Equation (51) can be shown to be identical to fuel consumption calculated using the annual method based on Equation (35). First, Equation (58), which is a rearrangement of Equation (51), can be simplified. Multiplying Equation (58) by HeatOrCool results in (HeatOrCool)² on the left hand side, which equals 1 for both heating and cooling seasons, and can thus be dropped from the equation. In addition, the sign on the first term on the right hand side of Equation (58) ([$UA^{Total}$ ($T^{Outdoor} - T^{Indoor}$)](H)) can be changed by reversing the order of the temperatures. Per Equation (9), the second term on the right hand side of the equation $$\left[\left[(250)\overline{P} + \overline{Electric}\left(\frac{3,412 \text{ Btu}}{1 \text{ kWh}}\right) + W\overline{Solar}\left(\frac{3,412 \text{ Btu}}{1 \text{ kWh}}\right)\right](H)\right]$$

equals internal gains ($Q^{Gains-Internal}$), which can be substituted into Equation (58). Finally, dividing the equation by HVAC efficiency $\eta^{HVAC}$ yields:

$$R^{HVAC}\overline{Status} = \left[(HeatOrCool)(UA^{Total})(\overline{T}^{Indoor} - \overline{T}^{Outdoor})(H) - (HeatOrCool)Q^{Gains-Internal}\right]\left(\frac{1}{\eta^{HVAC}}\right) \quad (59)$$

Equation (59), which is a simplification of Equation (58), can be used to calculate net savings in fuel, cost, and carbon emissions (environmental), as described, for instance, in commonly-assigned U.S. Patent application, entitled "System and Method for Estimating Indoor Temperature Time Series Data of a Building with the Aid of a Digital Computer," Ser. No. 15/096,185, filed Apr. 11, 2016, pending, the disclosure of which is incorporated by reference. Next, substituting Equation (24) into Equation (59):

$$R^{HVAC}\overline{Status}(H) = \left[(HeatOrCool)(UA^{Total})(\overline{T}^{Indoor} - \overline{T}^{Outdoor})(H) - (HeatOrCool)(HeatOrCool)(UA^{Balance\ Point}) \right. \quad (60)$$
$$\left. (\overline{T}^{Indoor} - \overline{T}^{Outdoor})(H)\right]\left(\frac{1}{\eta^{HVAC}}\right)$$

Once again, HeatOrCool² equals 1 for both heating and cooling seasons and thus is dropped. Equation (60) simplifies as:

$$R^{HVAC}\overline{Status}(H) = \frac{[HeatOrCool(UA^{Total}) - (UA^{Balance\ Point})](\overline{T}^{Indoor} - \overline{T}^{Outdoor})(H)}{\eta^{HVAC}} \quad (61)$$

Consider the heating season when HeatOrCool equals 1. Equation (61) simplifies as follows.

$$Q^{Fuel} = \frac{(UA^{Total} - UA^{Balance\ Point})(\overline{T}^{Indoor} - \overline{T}^{Outdoor})(H)}{\eta^{HVAC}} \quad (62)$$

Equation (62) illustrates total seasonal fuel consumption based on Equation (51) is identical to fuel consumption calculated using the annual method based on Equation (35).

Consider the cooling season when HeatOrCool equals −1. Multiply Equation (62) by the first part of the right hand side by −1 and reverse the temperatures, substitute −1 for HeatOrCool, and simplify:

$$Q^{Fuel} = \frac{(UA^{Total} + UA^{Balance\ Point})(\overline{T}^{Indoor} - \overline{T}^{Outdoor})(H)}{\eta^{HVAC}} \quad (63)$$

A comparison of Equations (62) and (63) shows that a leverage effect occurs that depends upon whether the season is for heating or cooling. Fuel requirements are decreased in the heating season because internal gains cover a portion of building losses (Equation (62)). Fuel requirements are increased in the cooling season because cooling needs to be provided for both the building's temperature gains and the internal gains (Equation (63)).

Maximum Indoor Temperature

Allowing consumers to limit the maximum indoor temperature to some value can be useful from a personal physical comfort perspective. The limit of maximum indoor temperature (step 134) can be obtained by taking the minimum of $T_{t+\Delta t}^{Indoor}$ and $T^{Indoor-Max}$, the maximum indoor temperature recorded for the building during the heating season. There can be some divergence between the annual and detailed time series methods when the thermal mass of the building is unable to absorb excess heat, which can then be used at a later time. Equation (57) becomes Equation (64) when the minimum is applied.

$$T_{t+\Delta t}^{Indoor} = \quad (64)$$
$$\text{Min}\left\{T^{Indoor-Max}, T_t^{Indoor} + \left[\frac{1}{M}\right]\left[UA^{Total}(T_t^{Outdoor} - T_t^{Indoor}) + (250)P_t + Electric_t\left(\frac{3,412\ \text{Btu}}{1\ \text{kWh}}\right) + WSolar_t\left(\frac{3,412\ \text{Btu}}{1\ \text{kWh}}\right) + (HeatOrCool)R^{HVAC}\eta^{HVAC}Status_t\right]\Delta t\right\}$$

Comparison to Annual Method (First Approach)

Two different approaches to calculating annual fuel consumption are described herein. The first approach, per Equation (35), is a single-line equation that requires six inputs. The second approach, per Equation (64), constructs a time series dataset of indoor temperature and HVAC system status. The second approach considers all of the parameters that are indirectly incorporated into the first approach. The second approach also includes the building's thermal mass and the specified maximum indoor temperature, and requires hourly time series data for the following variables: outdoor temperature, solar resource, internal electricity consumption, and occupancy.

Figure 15:
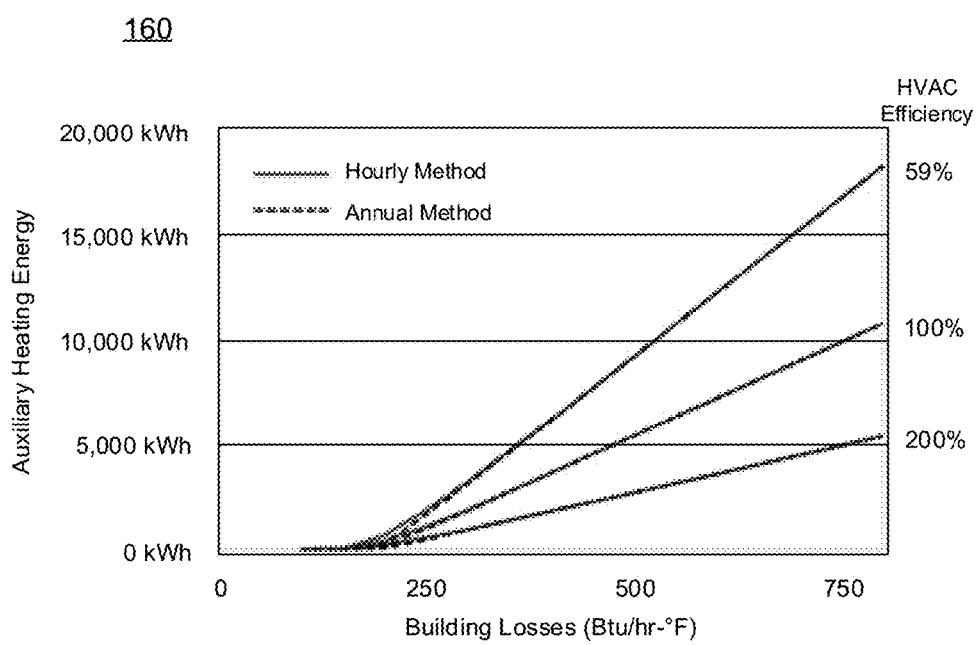
FIG. 15 is a graph showing, by way of example, a comparison of auxiliary heating energy requirements determined by the hourly approach versus the annual approach.

Both approaches were applied to the exemplary case, discussed supra, for the sample house in Napa, Calif. Thermal mass was 13,648 Btu/° F. and the maximum temperature was set at 72° F. The auxiliary heating energy requirements predicted by the two approaches was then compared. FIG. 15 is a graph 160 showing, by way of example, a comparison of auxiliary heating energy requirements determined by the hourly approach versus the annual approach. The x-axis represents total thermal conductivity, $UA^{Total}$ in units of Btu/hr-° F. The y-axis represents total heating energy. FIG. 15 uses the same format as the graph in FIG. 10 by applying a range of scenarios. The red line in the graph corresponds to the results of the hourly method. The dashed black line in the graph corresponds to the annual method. The graph suggests that results are essentially identical, except when the building losses are very low and some of the internal gains are lost due to house overheating, which is prevented in the hourly method, but not in the annual method.

Figure 16:
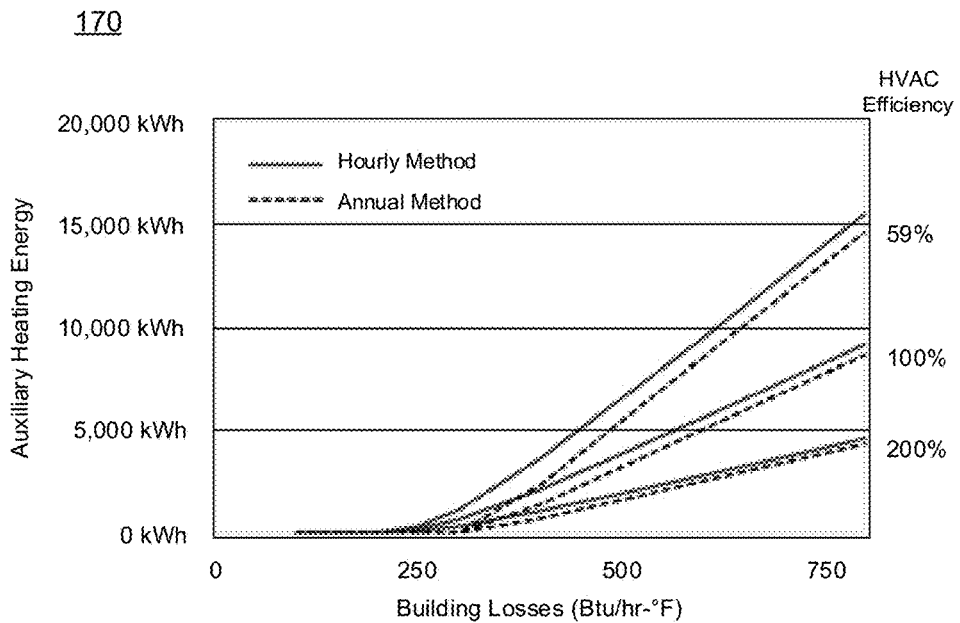
FIG. 16 is a graph showing, by way of example, a comparison of auxiliary heating energy requirements with the allowable indoor temperature limited to 2° F. above desired temperature of 68° F.
Figure 17:
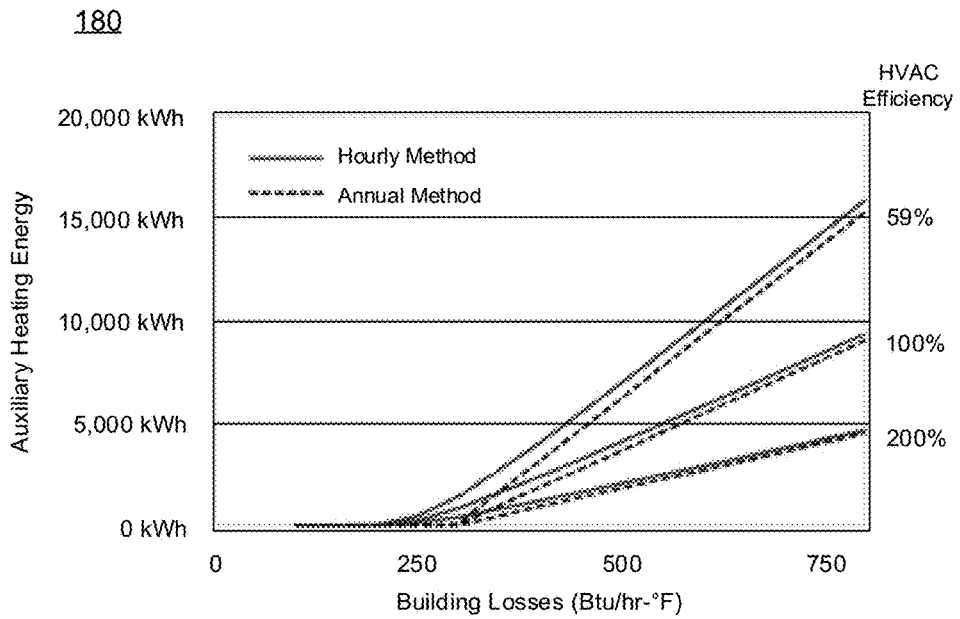
FIG. 17 is a graph showing, by way of example, a comparison of auxiliary heating energy requirements with the size of effective window area tripled from 2.5 m² to 7.5 m².

The analysis was repeated using a range of scenarios with similar results. FIG. 16 is a graph 170 showing, by way of example, a comparison of auxiliary heating energy requirements with the allowable indoor temperature limited to 2° F. above desired temperature of 68° F. Here, the only cases that found any meaningful divergence occurred when the maximum house temperature was very close to the desired indoor temperature. FIG. 17 is a graph 180 showing, by way of example, a comparison of auxiliary heating energy requirements with the size of effective window area tripled from 2.5 m² to 7.5 m². Here, internal gains were large by tripling solar gains and there was insufficient thermal mass to provide storage capacity to retain the gains.

The conclusion is that both approaches yield essentially identical results, except for cases when the house has inadequate thermal mass to retain internal gains (occupancy, electric, and solar).

Example

The performance of the tests described supra using measured data can be illustrated through an example. These tests were performed between 9 PM on Jan. 29, 2015 to 6 AM on Jan. 31, 2015 on a 35 year-old, 3,000 ft² house in Napa, Calif. This time period was selected to show that all of the tests could be performed in less than a day-and-a-half. In addition, the difference between indoor and outdoor temperatures was not extreme, making for a more challenging situation to accurately perform the tests.

FIG. 18 is a table 190 showing, by way of example, test data. The sub columns listed under "Data" present measured hourly indoor and outdoor temperatures, direct irradiance on a vertical south-facing surface (VDI), electricity consumption that resulted in indoor heat, and average occupancy. Electric space heaters were used to heat the house and the HVAC system was not operated. The first three short-duration tests, described supra, were applied to this data. The specific data used are highlighted in gray. FIG. 19 is a table 200 showing, by way of example, the statistics performed on the data in the table 190 of FIG. 18 required to calculate the three test parameters. $UA^{Total}$ was calculated using the data in the table of FIG. 10 and Equation (53). Thermal Mass (M) was calculated using $UA^{Total}$, the data in the table of FIG. 10, and Equation (54). Effective Window Area (W) was calculated using $UA^{Total}$, M, the data in the table of FIG. 10, and Equation (55).

These test parameters, plus a furnace rating of 100,000 Btu/hour and assumed efficiency of 56%, can be used to generate the end-of-period indoor temperature by substituting them into Equation (57) to yield:

$$T_{t+\Delta t}^{Indoor} = \quad (65)$$

$$T_t^{Indoor} + \left[\frac{1}{18,084}\right][429(T_t^{Outdoor} - T_t^{Indoor}) + (250)P_t + 3412$$

$$Electric_t + 11,600\ Solar_t + (1)(100,000)(0.56)Status_t]\Delta t$$

Figure 21:
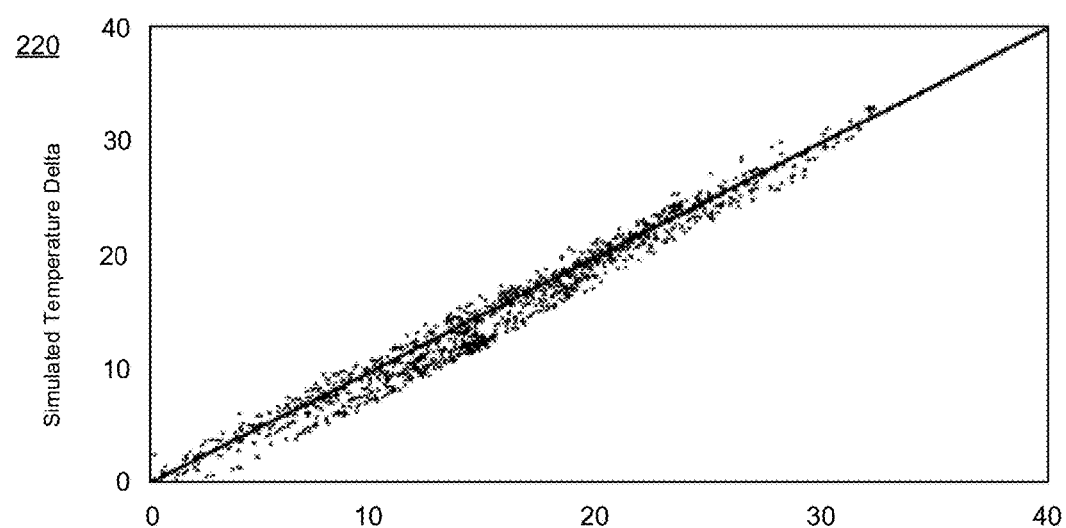
FIG. 21 is a graph showing, by way of example, simulated versus measured hourly temperature delta (indoor minus outdoor).

Indoor temperatures were simulated using Equation (65) and the required measured time series input datasets. Indoor temperature was measured from Dec. 15, 2014 to Jan. 31, 2015 for the test location in Napa, Calif. The temperatures were measured every minute on the first and second floors of the middle of the house and averaged. FIG. 20 is a graph 210 showing, by way of example, hourly indoor (measured and simulated) and outdoor (measured) temperatures. FIG. 21 is a graph 220 showing, by way of example, simulated versus measured hourly temperature delta (indoor minus outdoor). FIG. 20 and FIG. 21 suggest that the calibrated model is a good representation of actual temperatures.

Empirically Determining Infiltration Using a $CO_2$ Monitoring Device

As explained supra with reference to Equation (5), a building's total thermal conductivity $UA^{Total}$ equals heat loss or gain due to conduction plus infiltration. Being able to specifically determine infiltration is extremely empowering. The knowledge of the degree to which infiltration and conduction individually contribute to or adversely affect a home's total thermal conductivity enables consumers to improve total building envelope efficiency by selecting energy efficiency investments according to their specific needs to respectively achieve better sealing or insulation.

By way of background, the rate of increase of a tracer gas in a closed space equals the rate of addition of the tracer gas minus the rate of removal of the tracer gas. This relationship can be expressed in a differential equation that can then be solved for the concentration of the tracer gas at a given point in time. With slight modifications to the basic equation, the $CO_2$ concentration in parts per million (ppm) at time t can be expressed as:

$$C_t^{Inside} = \left[\frac{(P)(S)(10^6)}{nV}\right](1 - e^{-nt}) + C^{Outside} + (C_0^{Inside} - C^{Outside})e^{-nt} \quad (66)$$

where $C_0^{Inside}$ is the concentration of the gas (ppm) inside the building at the beginning of a test; $C_t^{Inside}$ is the concentration of the gas (ppm) inside the building at time t; $C_0^{Inside}$ is the concentration of the gas (ppm) inside the building at the beginning of a test; $C_0^{Outside}$ is the concentration of the gas (ppm) outside the building and does not have a time subscript because $C_0^{Outside}$ is assumed to be constant over time; P is the number of people in the building; S is the rate of addition of the $CO_2$ source gas in ft³ per person per hour; V is the volume of the building in ft³; n is the number of ACH; and t is time expressed in hours. The rate of addition of the $CO_2$ source gas that a person emits (S) when resting or having a low activity amount of work is estimated at 0.71 ft³ (i.e., 0.020 m³) of $CO_2$ per hour. See, e.g., http://www.engineeringtoobox.com/co2-persons-d_691.html, which is incorporated by reference.

In a further embodiment, infiltration can be empirically determined by measuring the number of ACH in a building through the use of a device that monitors $CO_2$ concentrations, such as a Netatmo Weather Station, manufactured by Netatmo, Boulogne-Billancourt, France. As the $CO_2$ concentration is monitored and measured, the device is interfaced with an application running on a remote mobile device, such as a smartphone, or other remotely interfaceable computational device, including a personal computer, notebook, or tablet computer, that enables the monitored $CO_2$ concentration and any other measured data, such as temperature, humidity, air quality, and sound level, to be regularly tracked, retrieved and recorded, displayed, and analyzed. Based on the change in $CO_2$ concentration over time, the infiltration component of total thermal conductivity can be determined; the conduction component of thermal conductivity can then be found by subtracting the $CO_2$ concentration measurement-based infiltration component from the building's total thermal conductivity $UA^{Total}$.

Ordinarily, the concentration of $CO_2$ inside of a building will change over time based on several factors, including:
Initial $CO_2$ concentration inside the building.
$CO_2$ concentration outside the building.
Amount of $CO_2$ added to the air inside the building as a result of occupants (or pets) breathing or, infrequently, other sources of $CO_2$.
The infiltration rate of the outside air entering the building.

Other factors causing the $CO_2$ concentration inside a building to change are possible. For instance, plants absorb $CO_2$, yet their impact on indoor $CO_2$ concentration is generally de minimus, unless there is a substantial number of indoor plants or the plants are of atypically large size, like mature trees. However, in the ordinary situation, an average number of indoor house plants will not significantly change $CO_2$ concentration more than the foregoing factors.

Empty Building Test

Infiltration, and therefore conduction, can be directly determined by empirically measuring $CO_2$ concentration in an empty building. FIG. 30 is a flow diagram showing a method 230 for determining infiltration of a building through empirical testing using a $CO_2$ concentration monitoring device, in accordance with a further embodiment. This test, referred to as the Empty Building Test, requires the use of a $CO_2$ concentration monitoring device that takes $CO_2$ concentration readings inside the empty building over time. The $CO_2$ concentration readings are electronically recorded, after which infiltration (based on ACH) and conduction (based on total thermal conductivity) can be determined using, for instance, a computing or mobile device, such as further described infra with reference to FIG. 29.

Prior to testing, a baseline of outdoor $CO_2$ concentration should be chosen (step 231). There are at least two options for manually making this determination. First, if only one $CO_2$ concentration monitoring device is available, the device can be temporarily placed outside the building for at least several hours to calibrate the device and measure outdoor $CO_2$ concentration before installing the device indoors. Second, if available, separate $CO_2$ concentration monitoring devices can be employed for indoor and outdoor uses; the outdoor device can be used to measure the outdoor $CO_2$ concentration. Note that the two devices will need to be checked against each other prior to deployment to ensure that they produce the same results under the same conditions. In lieu of actually taking a measurement, the outdoor $CO_2$ concentration can simply be assumed to be 400 ppm. Still other ways or devices to determine the outdoor $CO_2$ concentration are possible.

Next, a $CO_2$ concentration monitoring device is installed inside the building (step 232) and the initial indoor $CO_2$ concentration is determined and recorded by the device (step 233). Note that the indoor $CO_2$ concentration should be approximately equal to the outdoor $CO_2$ concentration. If the outdoor and indoor $CO_2$ concentrations vary by an appreciable margin, the source of the disparity should first be identified and, if possible, removed from inside the building, so that parity of indoor and outdoor $CO_2$ concentrations is achieved.

The concentration of indoor $CO_2$ is then increased from the initial measured indoor $CO_2$ concentration (step 234). There are at least three options for increasing the indoor $CO_2$ concentration. First, people could be brought in to occupy the building, so as to naturally increase the $CO_2$ concentration through their breathing. Second, the $CO_2$ concentration can be manually increased by obtaining dry ice (widely available at nominal cost); the dry ice is converted from solid to gaseous form by placing the dry ice in water. For instance, one pound of dry ice can produce 250 liters (0.25 $m^3$) of $CO_2$, which is equivalent to a dozen people breathing for one hour since each person produces 0.02 $m^3$ of $CO_2$ per hour at a nominal activity level. Last, $CO_2$ concentration can be manually increased by discharging a $CO_2$ fire extinguisher inside the building; the volume of $CO_2$ thus released would roughly correlate to the discharge capacity of the fire extinguisher. The cost of increasing $CO_2$ concentration in this manner would be the cost of recharging or replacing the $CO_2$ fire extinguisher.

Once the $CO_2$ concentration has been increased from the initial $CO_2$ concentration as measured, the sources causing any increase of the indoor $CO_2$ concentration are negated inside the building and monitoring begins (step 235). The test does not need to begin precisely when the sources are negated, so long as the test is started at some point thereafter. Note that, in this sense, "negated" simply means removing from the inside of the building any sources of indoor $CO_2$ concentration increase, which may be vacating the people brought in to occupy the building or eliminating sources of manual $CO_2$ concentration increase, such as dry ice or a $CO_2$ fire extinguisher.

The $CO_2$ concentration is then monitored and recorded over time, starting once the building has been vacated (step 236). The test can last as little as one hour. The monitoring and recording of the $CO_2$ concentration is stopped when the $CO_2$ concentration has stabilized (step 237), which occurs when the indoor $CO_2$ concentration is roughly equal to the outdoor $CO_2$ concentration as measured prior to testing, assuming that the indoor $CO_2$ concentration as initially measured was approximately equal to the outdoor $CO_2$ concentration or, alternatively, no further changes in $CO_2$ concentration are observed after a long lapse of time.

Based on the recorded $CO_2$ concentration measurements, infiltration (and therefore conduction) can be determined (step 238), as follows. First, the first term on the right hand side of Equation (66), $$\left[\frac{(P)(S)(10^6)}{nV}\right](1 - e^{-nt}),$$

will equal 0 because no additional $CO_2$ will have been added to the interior of the building once the sources causing any increase of the indoor $CO_2$ concentration are negated. Thus, Equation (66) can be simplified to:

$$C_t^{Inside} = C^{Outside} + (C_0^{Inside} - C^{Outside})e^{-n\,t} \qquad (67)$$

Second, infiltration, as represented by the number of ACH, can be determined by solving Equation (67) for n:

$$n = \ln\left(\frac{C_0^{Inside} - C^{Outside}}{C_t^{Inside} - C^{Outside}}\right)\left(\frac{1}{t}\right) \qquad (68)$$

Note that the solution is only valid under conditions where t is greater than 0 and t is not excessively large, where $C_t^{Inside} = C^{Outside}$. Last, conduction can be found by subtracting the infiltration from the building's total thermal conductivity.

Fully Occupied Building Equilibrium

In a still further embodiment, once the number of ACH has been measured using Equation (68), the result can be confirmed using long-term data. The approach is to evaluate $CO_2$ concentrations under steady-state, fully-occupied conditions, which occurs when time t is large. Under these conditions, Equation (66) simplifies to:

$$C_t^{Inside} = \left[\frac{(P)(S)(10^6)}{nV}\right] + C^{Outside} \quad (69)$$

Equation (69) provides an upper bound on estimated indoor $CO_2$ concentration. Thus, $\lceil C_t^{Inside} \rceil$ would provide a limit to indoor $CO_2$ concentration beyond which $C_t^{Inside}$ would not exceed. The equation can be used assuming that the number of people is known and remains fairly constant over time t, $CO_2$ addition per person can be estimated, and the volume of the building V can be determined.

Long Duration Test Validation

Equation (69) can be rearranged to calculate the number of ACH under steady-state, fully-occupied conditions if certain variables are known:

$$n = \left[\frac{(P)(S)}{(V)(10^6)}\right]\left(\frac{1}{C_t^{Inside} - C^{Outside}}\right) \quad (70)$$

Examples are discussed infra to compare the results generated by Equations (68) and (70).

Validation

Figure 23:
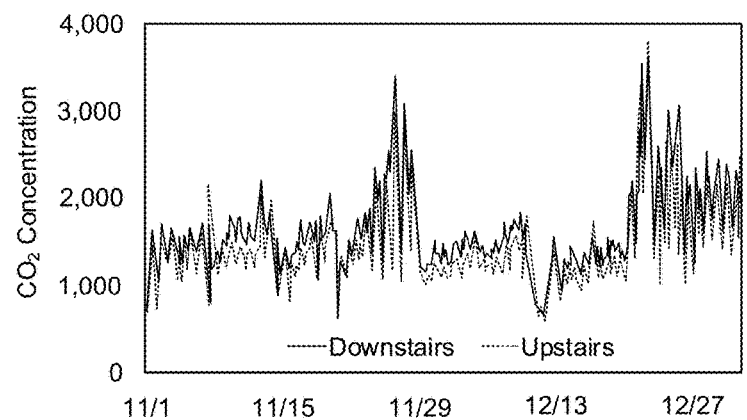
FIG. 23 is a graph showing, by way of example, a time series of $CO_2$ concentration levels inside a test house as measured every half-hour from Nov. 1 to Dec. 31, 2015.
Figure 24:
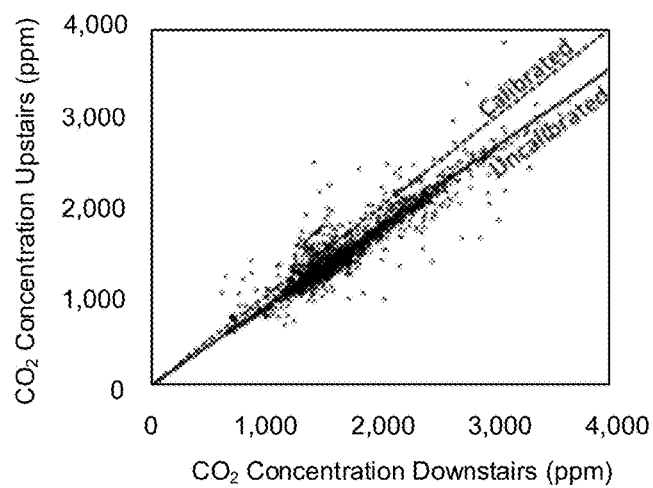
FIG. 24 is a graph showing, by way of example, the monitored $CO_2$ concentration as measured in locations upstairs and downstairs in the test house during the two-month period.

To validate the methodology, a $CO_2$ concentration monitoring device was installed in a test house in Napa, Calif. The test house is a well-sealed, 3,000 ft² house. FIG. 23 is a graph 240 showing, by way of example, a time series of $CO_2$ concentration levels inside a test house as measured every half-hour from Nov. 1 to Dec. 31, 2015. The x-axis represents the day of the month. The y-axis represents $CO_2$ concentration in ppm. The solid black line shows the $CO_2$ concentration measured downstairs and the dotted gray line shows the $CO_2$ concentration measured upstairs. One question is how many $CO_2$ concentration monitoring devices are required in a building to perform this type of test. The answer depends upon how well the $CO_2$ mixes throughout the building. FIG. 24 is a graph 250 showing, by way of example, the monitored $CO_2$ concentration as measured in locations upstairs and downstairs in the test house during the two-month period. The x- and y-axes represent $CO_2$ concentration in ppm. The solid black line shows the trend between the uncalibrated data and the dashed black line shows what the trend would have been if the devices had the same calibration. The data suggests that, while there is a small calibration difference between the data collected at the upstairs and downstairs locations, the half-hour measurements at the two different locations are linearly related to each other most of the time with only a 5% absolute error on a half-hour basis once the two measurements are correctly calibrated. Both sensors provide a good relative measurement of $CO_2$ concentration, which suggests that $CO_2$ mixes rather quickly throughout the building and that one device would have been sufficient to perform the test in this case.

Figure 25:
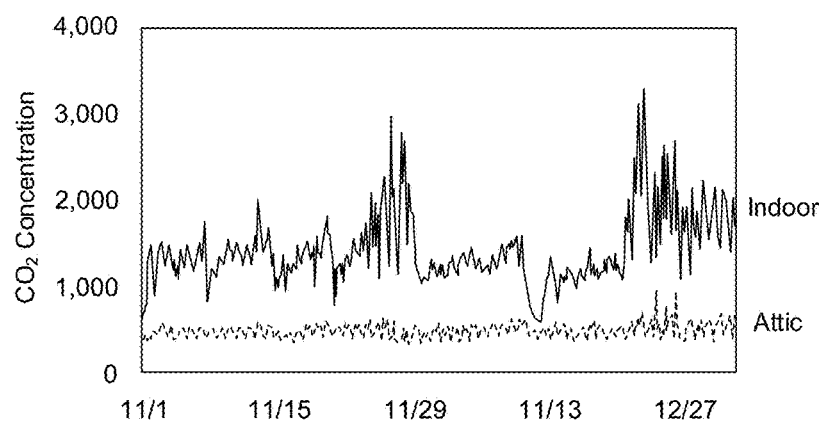
FIG. 25 is a graph showing, by way of example, a time series of $CO_2$ concentration levels inside and outside the test house as measured every half-hour from Nov. 1 to Dec. 31, 2015.

FIG. 25 is a graph 260 showing, by way of example, a time series of $CO_2$ concentration levels inside and outside the test house as measured every half-hour from Nov. 1 to Dec. 31, 2015. The x-axis represents the day of the month. The y-axis represents $CO_2$ concentration in ppm. The solid black line shows the indoor $CO_2$ concentration, as an average of upstairs and downstairs measurements, and the dotted gray line shows the concentration $CO_2$ measured in the attic, which is representative of the outdoor $CO_2$ concentration. The data suggests that there was a noticeable drop in indoor $CO_2$ concentration starting at around 9 am, which occurred when the test house's two occupants left for several days.

Figure 26:
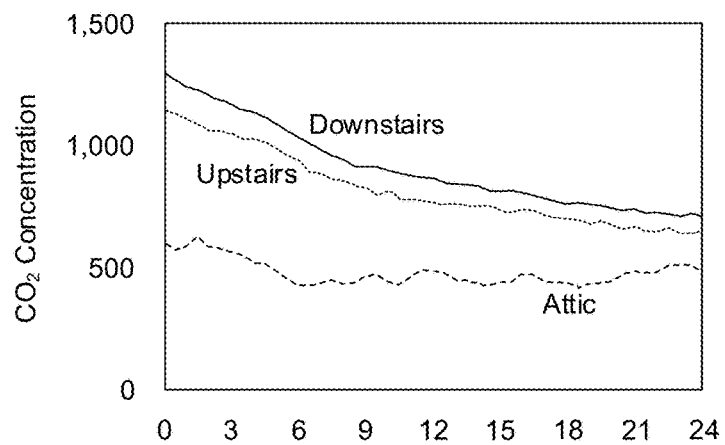
FIG. 26 is a graph showing, by way of example, a time series of $CO_2$ concentration levels inside and outside the test house as measured every half-hour for a 24-hour period on Dec. 10, 2015.

The absence of the occupants from the test house presented a good opportunity to perform the short-duration empty house test to see how many hours would be required to determine the air leakage rate in ACH. FIG. 26 is a graph showing, by way of example, a time series of $CO_2$ concentration levels inside and outside the test house as measured every half-hour for a 24-hour period on Dec. 10, 2015. The x-axis represents test duration in hours. The y-axis represents $CO_2$ concentration in ppm. The top line shows the $CO_2$ concentration measured downstairs. The middle line shows the $CO_2$ concentration measured upstairs. The bottom line shows the $CO_2$ concentration measured in the attic. The data have not been calibrated.

Figure 27:
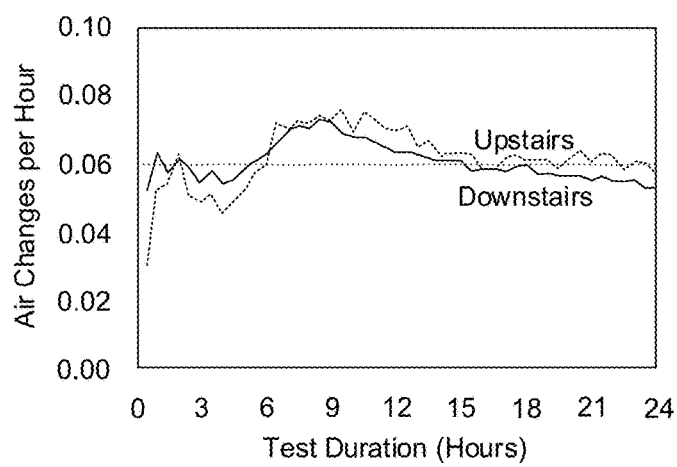
FIG. 27 is a graph showing, by way of example, a time series of numbers of ACH for a 24-hour period on Dec. 10, 2015.

Based on the recorded data, the number of ACH was determined using Equation (68) with $CO_2$ concentration graphed as a function of time. FIG. 27 is a graph 280 showing, by way of example, a time series of numbers of ACH for a 24-hour period on Dec. 10, 2015. The x-axis represents test duration in hours. The y-axis represents ACH. Based on the recorded data, the average $CO_2$ concentration in the attic was 483 ppm. The initial $CO_2$ concentrations upstairs and downstairs respectively were 1,144 ppm and 1,297 ppm. The $CO_2$ concentration downstairs one hour after the test began was 1,247 ppm. Thus, according to Equation (68), the house had an ACH of 0.063 (0.063=ln((1,297−483)/(1,247−483))(1/1)) one hour after the test was initiated. While there is some variation based on the location and duration of the test, results indicate that the house has an air leakage rate of about 0.06 ACH. Note that there is minimal sensitivity to outdoor $CO_2$ concentration. Assuming, for example, that the outdoor $CO_2$ concentration was a default value of 400 ppm, rather than the measured value of 483 ppm in the Attic, the house would have had an ACH of 0.057 (0.057=ln((1,297−400)/(1,247−400))(1/1)) one hour after the test initiated, which still rounds up to 0.06. These findings suggest that acceptable results can be obtained by performing a one-hour test and assuming a default value for outdoor $CO_2$ concentration.

Further Validation

Equation (69) can be used to validate the accuracy of test results by comparing actual measurements to steady state conditions. The test house is 3,000 ft² with an average ceiling height of eight feet to create a volume of 24,000 ft³. Thus, assuming that the two occupants would emit 1.42 ft³ of $CO_2$ per hour, the steady-state $CO_2$ equilibrium for equals 1,483 ppm:

$$C_t^{Inside} = \left[\frac{(P)(S)(10^6)}{nV}\right] + C^{Outside} = \quad (71)$$

$$497 + \left[\frac{(2 \text{ people})\left(0.71\frac{ft^3}{person}hour\right)(10^6)}{\left(0.06 \text{ air}\frac{change}{hour}\right)(24,000 \text{ ft}^3)}\right] = 1,483$$

Figure 28:
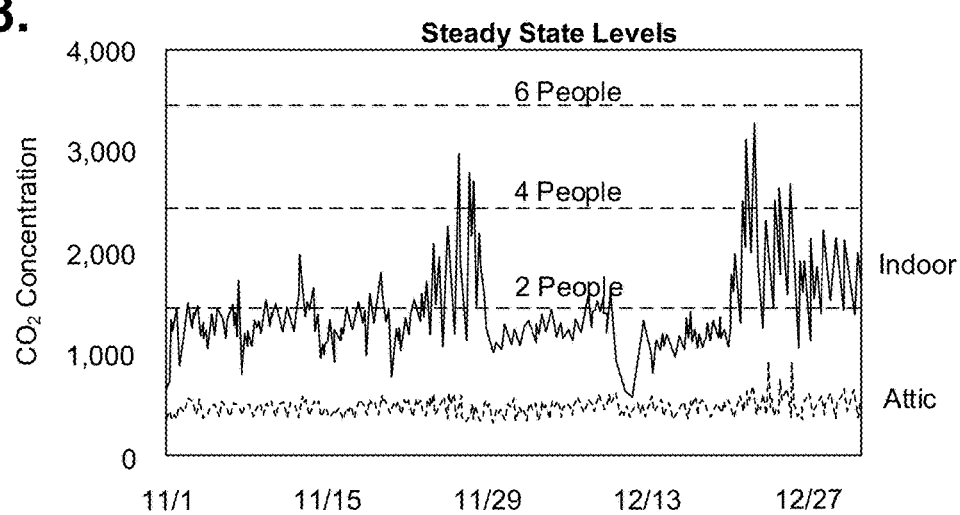
FIG. 28 is a graph showing, by way of example, a steady state $CO_2$ concentration levels inside and outside the test house as projected from Nov. 1 to Dec. 31, 2015 for two, four, and six people.

Steady state $CO_2$ equilibrium can be estimated for larger bodies of people. FIG. 28 is a graph showing, by way of example, a steady state $CO_2$ concentration levels inside and outside the test house as projected from Nov. 1 to Dec. 31, 2015 for two, four, and six people. The projected data corresponds nicely with actual conditions. For instance, the house was occupied by two people for most of the time period under consideration, except for the Thanksgiving and Christmas holidays, where the house contained up to six occupants, and the weeks after Christmas, where the house contained six occupants. The house had no external ventilation during this time.

Energy Consumption Modeling System

Figure 29:
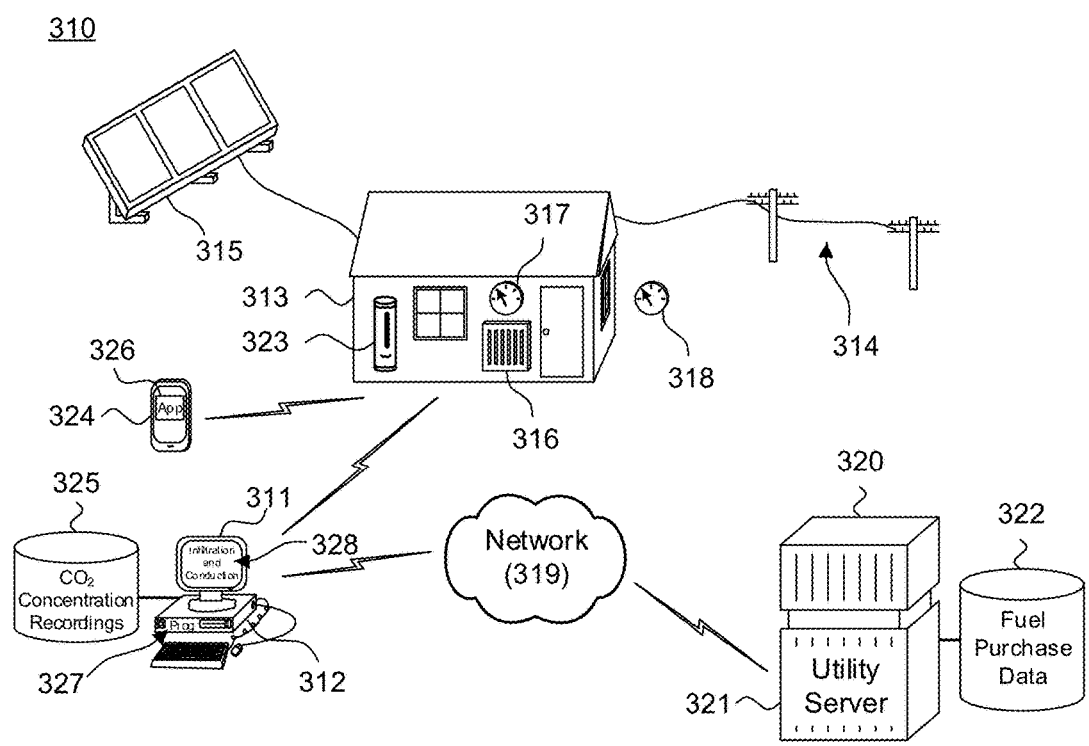
FIG. 29 is a block diagram showing a system for determining infiltration of a building through empirical testing using a $CO_2$ concentration monitoring device, in accordance with a further embodiment.

Modeling energy consumption for heating (or cooling) on an annual (or periodic) basis, as described supra with reference FIG. 1, and on an hourly (or interval) basis, as described supra beginning with reference to FIG. 11, can be performed with the assistance of a computer, or through the use of hardware tailored to the purpose. In a further embodiment, the number of ACH can be empirically measured under actual operating conditions, as described supra beginning with reference to FIG. 22, which enables infiltration and conduction to be directly determined; this methodology can be performed with the assistance of a $CO_2$ concentration monitoring device and a computer, or through the use of hardware tailored to the purpose. FIG. 29 is a block diagram showing a system 310 for determining infiltration of a building 313 through empirical testing using a $CO_2$ concentration monitoring device, in accordance with a further embodiment. A computer system 311, such as a personal, notebook, or tablet computer, as well as a smartphone or programmable mobile device, can be programmed to execute software programs 312 that operate autonomously or under user control, as provided through user interfacing means, such as a monitor, keyboard, and mouse. The computer system 311 includes hardware components conventionally found in a general purpose programmable computing device, such as a central processing unit, memory, input/output ports, network interface, and non-volatile storage, and execute the software programs 312, as structured into routines, functions, and modules. In addition, other configurations of computational resources, whether provided as a dedicated system or arranged in client-server or peer-to-peer topologies, and including unitary or distributed processing, communications, storage, and user interfacing, are possible.

In one embodiment, to perform the first approach, the computer system 311 needs data on heating losses and heating gains, with the latter separated into internal heating gains (occupant, electric, and solar) and auxiliary heating gains. The computer system 311 may be remotely interfaced with a server 320 operated by a power utility or other utility service provider 321 over a wide area network 319, such as the Internet, from which fuel purchase data 322 can be retrieved. Optionally, the computer system 311 may also monitor electricity 314 and other metered fuel consumption, where the meter is able to externally interface to a remote machine, as well as monitor on-site power generation, such as generated by a photovoltaic system 315. The monitored fuel consumption and power generation data can be used to create the electricity and heating fuel consumption data and historical solar resource and weather data. The computer system 311 then executes a software program 312 to determine annual (or periodic) heating fuel consumption based on the empirical approach described supra with reference to FIG. 1.

In a further embodiment, to assist with the empirical tests performed in the second approach, the computer system 311 can be remotely interfaced to a heating source 316 and a thermometer 317 inside a building 313 that is being analytically evaluated for thermal performance, thermal mass, effective window area, and HVAC system efficiency. In a further embodiment, the computer system 311 also remotely interfaces to a thermometer 318 outside the building 163, or to a remote data source that can provide the outdoor temperature. The computer system 311 can control the heating source 316 and read temperature measurements from the thermometer 317 throughout the short-duration empirical tests. In a further embodiment, a cooling source (not shown) can be used in place of or in addition to the heating source 316. The computer system 311 then executes a software program 312 to determine hourly (or interval) heating fuel consumption based on the empirical approach described supra with reference to FIG. 11.

In a still further embodiment, a $CO_2$ concentration monitoring device 323 monitors $CO_2$ concentration inside the building 313 and may also be used to measure $CO_2$ concentration outside the building 313, depending upon the testing configuration. The $CO_2$ concentration monitoring device 323 can be remotely interfaced to a mobile device 324, such as a smartphone, or the computer system 311. The $CO_2$ concentration monitoring device 323 monitors and records the $CO_2$ concentration during the test and the $CO_2$ concentration recordings 325 are obtained by the mobile device 324. The mobile device 324 (or computer system 313) then executes an application ("App") 326 (or program 327) to determine infiltration and conduction 328 based on the empirical approach described supra with reference to FIG. 22.

Applications

The two approaches to estimating energy consumption for heating (or cooling), hourly and annual, provide a powerful set of tools that can be used in various applications. A non-exhaustive list of potential applications will now be discussed. Still other potential applications are possible.

Application to Homeowners

Both of the approaches, annual (or periodic) and hourly (or interval), reformulate fundamental building heating (and cooling) analysis in a manner that can divide a building's thermal conductivity into two parts, one part associated with the balance point resulting from internal gains and one part associated with auxiliary heating requirements. These two parts provide that:

Consumers can compare their house to their neighbors' houses on both a total thermal conductivity $UA^{Total}$ basis and on a balance point per square foot basis. These two numbers, total thermal conductivity $UA^{Total}$ and balance point per square foot, can characterize how well their house is doing compared to their neighbors' houses. The comparison could also be performed on a neighborhood- or city-wide basis, or between comparably built houses in a subdivision. Other types of comparisons are possible.

As strongly implied by the empirical analyses discussed supra, heater size can be significantly reduced as the interior temperature of a house approaches its balance point temperature. While useful from a capital cost perspective, a heater that was sized based on this implication may be slow to heat up the house and could require long lead times to anticipate heating needs. Temperature and solar forecasts can be used to operate the heater by application of the two approaches described supra, so as to optimize operation and minimize consumption. For example, if the building owner or occupant knew that the sun was going to start adding a lot of heat to the building in a few hours, he may choose to not have the heater turn on. Alternatively, if the consumer was using a heater with a low power rating, he would know when to turn the heater off to achieve desired preferences.

Application to Building Shell Investment Valuation

The economic value of heating (and cooling) energy savings associated with any building shell improvement in any building has been shown to be independent of building type, age, occupancy, efficiency level, usage type, amount of internal electric gains, or amount solar gains, provided that fuel has been consumed at some point for auxiliary heating. As indicated by Equation (47), the only information required to calculate savings includes the number of hours that define the winter season; average indoor temperature; average outdoor temperature; the building's HVAC system efficiency (or coefficient of performance for heat pump systems); the area of the existing portion of the building to be upgraded; the R-value of the new and existing materials; and the average price of energy, that is, heating fuel. This finding means, for example, that a high efficiency window replacing similar low efficiency windows in two different buildings in the same geographical location for two different customer types, for instance, a residential customer versus an industrial customer, has the same economic value, as long as the HVAC system efficiencies and fuel prices are the same for these two different customers.

This finding vastly simplifies the process of analyzing the value of building shell investments by fundamentally altering how the analysis needs to be performed. Rather than requiring a full energy audit-style analysis of the building to assess any the costs and benefits of a particular energy efficiency investment, only the investment of interest, the building's HVAC system efficiency, and the price and type of fuel being saved are required.

As a result, the analysis of a building shell investment becomes much more like that of an appliance purchase, where the energy savings, for example, equals the consumption of the old refrigerator minus the cost of the new refrigerator, thereby avoiding the costs of a whole house building analysis. Thus, a consumer can readily determine whether an acceptable return on investment will be realized in terms of costs versus likely energy savings. This result could be used in a variety of places:

Direct display of economic impact in ecommerce sites. A Web service that estimates economic value can be made available to Web sites where consumers purchase building shell replacements. The consumer would select the product they are purchasing, for instance, a specific window, and would either specify the product that they are replacing or a typical value can be provided. This information would be submitted to the Web service, which would then return an estimate of savings using the input parameters described supra.

Tools for salespeople at retail and online establishments.

Tools for mobile or door-to-door sales people.

Tools to support energy auditors for immediate economic assessment of audit findings. For example, a picture of a specific portion of a house can be taken and the dollar value of addressing problems can be attached.

Have a document with virtual sticky tabs that show economics of exact value for each portion of the house. The document could be used by energy auditors and other interested parties.

Available to companies interacting with new building purchasers to interactively allow them to understand the effects of different building choices from an economic (and environmental) perspective using a computer program or Internet-based tool.

Enable real estate agents working with customers at the time of a new home purchase to quantify the value of upgrades to the building at the time of purchase.

Tools to simplify the optimization problem because most parts of the problem are separable and simply require a rank ordering of cost-benefit analysis of the various measures and do not require detailed computer models that applied to specific houses.

The time to fix the insulation and ventilation in a homeowner's attic is when during reroofing. This result could be integrated into the roofing quoting tools.

Incorporated into a holistic zero net energy analysis computer program or Web site to take an existing building to zero net consumption.

Integration into tools for architects, builders, designers for new construction or retrofit. Size building features or HVAC system. More windows or less windows will affect HVAC system size.

Application to Thermal Conductivity Analysis

A building's thermal conductivity can be characterized using only measured utility billing data (natural gas and electricity consumption) and assumptions about effective window area, HVAC system efficiency and average indoor building temperature. This test could be used as follows:

Utilities lack direct methods to measure the energy savings associated with building shell improvements. Use this test to provide a method for electric utilities to validate energy efficiency investments for their energy efficiency programs without requiring an on-site visit or the typical detailed energy audit. This method would help to address the measurement and evaluation (M&E) issues currently associated with energy efficiency programs.

HVAC companies could efficiently size HVAC systems based on empirical results, rather than performing Manual J calculations or using rules of thumb. This test could save customers money because Manual J calculations require a detailed energy audit. This test could also save customers capital costs since rules of thumb typically oversize HVAC systems, particularly for residential customers, by a significant margin.

A company could work with utilities (who have energy efficiency goals) and real estate agents (who interact with customers when the home is purchased) to identify and target inefficient homes that could be upgraded at the time between sale and occupancy. This approach greatly reduces the cost of the analysis, and the unoccupied home offers an ideal time to perform upgrades without any inconvenience to the homeowners.

Goals could be set for consumers to reduce a building's heating needs to the point where a new HVAC system is avoided altogether, thus saving the consumer a significant capital cost.

Application to Building Performance Studies

A building's performance can be fully characterized in terms of four parameters using a suite of short-duration (several day) tests. The four parameters include thermal conductivity, that is, heat losses, thermal mass, effective window area, and HVAC system efficiency. An assumption is made about average indoor building temperature. These (or the previous) characterizations could be used as follows:

Utilities could identify potential targets for building shell investments using only utility billing data. Buildings could be identified in a two-step process. First, thermal conductivity can be calculated using only electric and natural gas billing data, making the required assumptions presented supra. Buildings that pass this screen could be the focus of a follow-up, on-site, short-duration test.

The results from this test suite can be used to generate detailed time series fuel consumption data (either natural gas or electricity). This data can be combined with an economic analysis tool, such as the PowerBill service (http://www.cleanpower.com/products/powerbill/), a software service offered by Clean Power Research, L.L.C., Napa, Calif., to calculate the economic impacts of the changes using detailed, time-of-use rate structures.

Application to "Smart" Thermostat Users

The results from the short-duration tests, as described supra with reference to FIG. 4, could be combined with measured indoor building temperature data collected using an Internet-accessible thermostat, such as a Nest thermostat device or a Lyric thermostat device, cited supra, or other so-called "smart" thermostat devices, thereby avoiding having to make assumptions about indoor building temperature. The building characterization parameters could then be combined with energy investment alternatives to educate consumers about the energy, economic, and environmental benefits associated with proposed purchases.

Applications of $CO_2$ Monitoring Device

The ability to empirically determine infiltration and conduction through a widely-available, low cost $CO_2$ monitoring device is particularly beneficial to consumers, who become empowered with the knowledge of the degree to which infiltration and conduction individually contribute to or adversely affect their home's total thermal conductivity. Thus, consumers are better able to improve total building envelope efficiency by selecting energy efficiency investments according to their specific needs to achieve better sealing or insulation.

A non-exhaustive list of potential applications of the $CO_2$ monitoring device will now be discussed. Still other potential applications are possible.

Monitoring building occupancy once air leakage rate is known to verify employee attendance; fewer $CO_2$ sensors would be required than occupancy sensors because they do not require line-of-site placement.

Controlling the operation of mechanical ventilation systems based on $CO_2$ to save energy, rather than continuously running heat exchangers or other ventilation devices.

While the invention has been particularly shown and described as referenced to the embodiments thereof, those skilled in the art will understand that the foregoing and other changes in form and detail may be made therein without departing from the spirit and scope.

What is claimed is:

1. A system for determining infiltration of a building through empirical testing using a $CO_2$ concentration monitoring device, comprising:
   a $CO_2$ concentration monitoring device provided inside a building under test and operable to determine and record initial $CO_2$ concentration, and further operable to measure and record further $CO_2$ concentrations inside the building subsequent to an increase in $CO_2$ concentration over the initial $CO_2$ concentration and a negation of sources causing the increase in the $CO_2$ concentration inside the building until the further $CO_2$ concentrations stabilize; and
   a computer comprising a processor configured to execute code in a memory, the code comprising:
   a baseline $CO_2$ concentration applicable to outside the building;
   a total thermal conductivity of the building;
   an infiltration module configured to determine infiltration of the building based on a number of air changes as a function of the difference of the initial $CO_2$ concentration less the baseline $CO_2$ concentration over one or more of the further $CO_2$ concentration at a given time less the baseline $CO_2$ concentration and the given time; and
   a conduction module configured to determine conduction of the building as the difference of the total thermal conductivity less the infiltration of the building, wherein at least one improvement to a shell of the building is performed based on the infiltration and the conduction.

2. A system according to claim 1, wherein the number of air changes n is determined in accordance with:

$$n = \ln\left(\frac{C_0^{Inside} - C^{Outside}}{C_t^{Inside} - C^{Outside}}\right)\left(\frac{1}{t}\right)$$

where $C_0^{Inside}$ is the initial $CO_2$ concentration; $C_t^{Inside}$ is the further $CO_2$ concentration at time t; $C^{Outside}$ is the baseline $CO_2$ concentration; and t is time expressed in hours.

3. A system according to claim 1, further comprising:
   the infiltration module further configured to limit the further $CO_2$ concentrations as recorded during the test by the $CO_2$ concentration monitoring device to an upper bound indoor $CO_2$ concentration,
   wherein the upper bound indoor $CO_2$ concentration was measured under steady-state, fully-occupied conditions inside the building.

4. A system according to claim 3, wherein the upper bound indoor $CO_2$ concentration $\lceil C_t^{Inside} \rceil$ at time t expressed in hours is determined in accordance with:

$$\lceil C_t^{Inside} \rceil = \left[\frac{(P)(S)(10^6)}{nV}\right] + C^{Outside}$$

where $C^{Outside}$ is the baseline $CO_2$ concentration; P is the number of people in the building; S is the rate of addition of the $CO_2$ source gas in ft³ per person per hour; V is the volume of the building in ft³; and n is the number of air changes per hour.

5. A system according to claim 1, further comprising:
   the infiltration module further configured to determine the infiltration of the building based on a number of air changes as a function of steady-state, fully-occupied conditions inside the building.

6. A system according to claim 5, wherein the number of air changes n is determined in accordance with:

$$n = \left[\frac{(P)(S)}{(V)(10^6)}\right]\left(\frac{1}{C_t^{Inside} - C^{Outside}}\right)$$

where P is the number of people in the building; S is the rate of addition of the $CO_2$ source gas in ft³ per person per hour; V is the volume of the building in ft³; $C_t^{Inside}$ is the further $CO_2$ concentration at time t; $C^{Outside}$ is the baseline $CO_2$ concentration; and t is time expressed in hours.

7. A system according to claim 1,
   wherein the $CO_2$ concentration monitoring device is remotely interfaced to the computer.

8. A system according to claim 1, further comprising:
   a testing ensemble configured to find the total thermal conductivity, thermal mass, and effective window area for the building through a series of sequentially-performed empirical tests, each successive empirical test building on findings of the earlier empirical tests.

9. A system according to claim 1, the baseline $CO_2$ concentration further comprising at least one of:
   prior to measuring and recording the further $CO_2$ concentrations, the $CO_2$ concentration monitoring device outside the building being operable to be calibrated and further operable to record the $CO_2$ concentration upon completion of the calibration as the baseline $CO_2$ concentration;
   a plurality of $CO_2$ concentration monitoring devices, one of which is operable to measure and record the further $CO_2$ concentrations and the other of which being operable to record the $CO_2$ concentration outside the building as the baseline $CO_2$ concentration; and
   the baseline $CO_2$ concentration assumed to be 400 ppm.

10. A system according to claim 1, the increase in $CO_2$ concentration further comprising at least one of:
    one or more people being introduced into the building;
    a known quantity of dry ice being converted into a gaseous form inside the building; and
    a $CO_2$ fire extinguisher of known capacity being discharged inside the building.

11. A method for determining infiltration of a building through empirical testing using a $CO_2$ concentration monitoring device, comprising the steps of:
    choosing by a computer comprising a processor a baseline $CO_2$ concentration outside a building under test;
    obtaining by the computer a total thermal conductivity of the building;
    determining and recording initial $CO_2$ concentration inside the building using a $CO_2$ concentration monitoring device;
    increasing $CO_2$ concentration over the initial $CO_2$ concentration;
    negating sources causing increase in the $CO_2$ concentration inside the building and thereafter measuring and recording further $CO_2$ concentrations inside the building using the $CO_2$ concentration monitoring device until the further $CO_2$ concentrations stabilize;
    determining by the computer infiltration of the building based on a number of air changes as a function of the difference of the initial $CO_2$ concentration less the baseline $CO_2$ concentration over one or more of the further $CO_2$ concentration at a given time less the baseline $CO_2$ concentration and the given time; and
    determining by the computer conduction of the building as the difference of the total thermal conductivity less the infiltration of the building, wherein at least one improvement to a shell of the building is performed based on the infiltration and the conduction.

12. A method according to claim 11, wherein the number of air changes n is determined in accordance with:

$$n = \ln\left(\frac{C_0^{Inside} - C^{Outside}}{C_t^{Inside} - C^{Outside}}\right)\left(\frac{1}{t}\right)$$

where $C_0^{Inside}$ is the initial $CO_2$ concentration; $C_t^{Inside}$ is the further $CO_2$ concentration at time 1; $C^{Outside}$ is the baseline $CO_2$ concentration; and t is time expressed in hours.

13. A method according to claim 11, further comprising the step of:
    limiting the further $CO_2$ concentrations as recorded during the test by the $CO_2$ concentration monitoring device to an upper bound indoor $CO_2$ concentration,
    wherein the upper bound indoor $CO_2$ concentration was measured under steady-state, fully-occupied conditions inside the building.

14. A method according to claim 13, wherein the upper bound indoor $CO_2$ concentration $\lceil C_t^{Inside} \rceil$ at time t expressed in hours is determined in accordance with:

$$\lceil C_t^{Inside} \rceil = \left[\frac{(P)(S)(10^6)}{nV}\right] + C^{Outside}$$

where $C^{Outside}$ is the baseline $CO_2$ concentration; P is the number of people in the building; S is the rate of addition of the $CO_2$ source gas in ft$^3$ per person per hour; V is the volume of the building in ft$^3$; and n is the number of air changes per hour.

15. A method according to claim 11, further comprising the step of:
    determining the infiltration of the building based on a number of air changes as a function of steady-state, fully-occupied conditions inside the building.

16. A method according to claim 15, wherein the number of air changes n is determined in accordance with:

$$n = \left[\frac{(P)(S)}{(V)(10^6)}\right]\left(\frac{1}{C_t^{Inside} - C^{Outside}}\right)$$

where P is the number of people in the building; S is the rate of addition of the $CO_2$ source gas in ft$^3$ per person per hour; V is the volume of the building in ft$^3$; $C_t^{Inside}$ is the further $CO_2$ concentration at time t; $C^{Outside}$ is the baseline $CO_2$ concentration; and t is time expressed in hours.

17. A method according to claim 11,
    wherein the $CO_2$ concentration monitoring device is remotely interfaced to the computer.

18. A method according to claim 1, further comprising the step of:
    finding the total thermal conductivity, thermal mass, and effective window area for the building through a series of sequentially-performed empirical tests, each successive empirical test building on findings of the earlier empirical tests.

19. A method according to claim 11, the step of choosing the baseline $CO_2$ concentration further comprising at least one of the steps of:
    prior to measuring and recording the further $CO_2$ concentrations, calibrating the $CO_2$ concentration monitoring device outside the building and recording the $CO_2$ concentration upon completion of the calibration as the baseline $CO_2$ concentration;
    calibrating a plurality of $CO_2$ concentration monitoring devices, one of which measuring and recording the further $CO_2$ concentrations and the other of which recording the $CO_2$ concentration outside the building as the baseline $CO_2$ concentration; and
    assuming the baseline $CO_2$ concentration to be 400 ppm.

20. A method according to claim 11, the step of increasing $CO_2$ concentration further comprising at least one of the steps of:
- introducing one or more people into the building;
- converting a known quantity of dry ice into a gaseous form inside the building; and
- discharging a $CO_2$ fire extinguisher of known capacity inside the building.

* * * * *